US006391569B1

(12) United States Patent
Grieve et al.

(10) Patent No.: US 6,391,569 B1
(45) **Date of Patent: *May 21, 2002**

(54) **METHOD TO DETECT *DIROFILARIA IMMITIS* INFECTION**

(75) Inventors: Robert B. Grieve, Fort Collins; Glenn R. Frank, Wellington; Roy R. Mondesire, Boulder; James P. Porter; Nancy Wisnewski, both of Fort Collins, all of CO (US)

(73) Assignee: Heska Corporation, Fort Collins, CO (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/715,628

(22) Filed: Sep. 18, 1996

(51) Int. Cl.$^7$ ..................... G01N 33/53; G01N 33/569; G01N 33/544; G01N 33/543

(52) U.S. Cl. .................... 435/7.22; 435/7.92; 435/7.93; 435/7.94; 435/7.95; 435/7.1; 435/69.1; 435/342; 530/350; 530/387.1; 530/388.6; 530/403; 424/191.1; 424/192.1; 424/269.1; 424/151.1; 436/501; 436/518; 436/528

(58) Field of Search .............................. 435/7.22, 7.92, 435/7.93, 7.94, 7.95, 7.1, 69.1, 342, 598; 530/350, 387.1, 388.6, 403; 424/191.1, 192.1, 269.1, 151.1

(56) References Cited

U.S. PATENT DOCUMENTS

| | | | | |
|---|---|---|---|---|
| 4,657,850 A | | 4/1987 | Grieve | |
| 4,789,631 A | | 12/1988 | Maggio | 435/7 |
| 4,839,275 A | | 6/1989 | Weil | |
| 4,962,035 A | | 10/1990 | Leder et al. | |
| 5,415,994 A | | 5/1995 | Imrich et al. | |
| 5,424,193 A | | 6/1995 | Pronovost et al. | |
| 5,492,695 A | | 2/1996 | Grieve et al. | 424/265.1 |
| 5,866,126 A | * | 2/1999 | Tripp et al. | |
| 5,945,294 A | * | 8/1999 | Frank et al. | |
| 5,977,306 A | * | 11/1999 | Grieve et al. | |
| 6,103,484 A | * | 8/2000 | Carlow et al. | |

FOREIGN PATENT DOCUMENTS

| | | |
|---|---|---|
| WO | WO 94/01775 | 1/1994 |
| WO | WO 94/29696 | 12/1994 |
| WO | WO 96/32641 | 9/1996 |

OTHER PUBLICATIONS

Reference A T: Poster Presentation at the Edna Clark McConnell Foundation Meeting of Apr. 10–13, 1994.*

Villanueva et al, Am. J. Trop. Med. Hyg., 48/4:536–541, 1993.*

Yamagata et al. Vet. Parasitol. 1992 vol. 44, 223–245.*

Paxton et al (1993) Infect & Immunity, vol. 61, 2827–2833.*

Boto, et al., "Homologous and Distinctive Antigens of *Onchocerca volvulus* and *Dirofilaria immitis*: Detection by an Enzyme–linked Immuno–inhibition Assay," 1984, pp. 981–987, *The Journal of Immunology 133:2*.

Chandrashekar, et al., "Evaluation of Recombinant Antigens Singly and Combined for Diagnosis of *Onchocerciasis*," 1994, p. 192, Abstract of *Trop. Med.* Meeting.

Chandrashekar, et al., "Molecular Cloning and Characterization of Recombinant Parasite Antigens for Immunodiagnosis of Onchocerciasis," 1991, pp. 1460–1466, *J. Clin. Invest. 88*.

Dissanayake, et al., "Molecular cloning and serological characterization of a *Brugia malayi* pepsin inhibitor homolog," 1993, pp. 143–146, *Molecular and Biochemical Parasitology 62*.

Hong, et al., "A Promising Recombinant Antigen for the Early Detection of Heartworm Infection," 1995, pp. 141–146, *Proceedings of the Heartworm Symposium, American Heartworm Society*.

Hong, et al., Cloning and expressions of DiT33 from *Dirofilaria immitis*: a specific and early marker of heartworm infection, 1996, pp. 331–338, *Parasitology 112*.

Hong, et al., "Molecular Cloning of a Pepsin Inhibitor Homolog From *Dirofilaria immitis* (DiT33) With Diagnostic Potential for Heartworm Infection," 1994, Abstract of *Amer. Soc. Top. Med. Hyg.* Meeting, pp. 191–192.

Lucius, et al., "Characterization of an Immunodominant *Onchocerca volvulus* Antigen With Patient Sera and a Monoclonal Antibody," 1988, pp. 1505–1510, *J. Exp. Med. 167*.

Lucius, et al., "Molecular Cloning of an Immunodominant Antigen of *Onchocerca volvulus*, " 1988, pp. 1199–1204, *J. Exp. Med. 168*.

Lucius, et al., "Specific and sensitive IgG4 immunodiagnosis of onchocerciasis with a recombinant 33kD *Onchocerca volvulus* protein (Ov33)," 1992, pp. 139–145, *Trop. Med. Parasitol. 43*.

Lucius, et al., "Studies on Antigens of the Rodent Filaria *Acanthocheilonema viteae* with Homology to Antigens of *Onchocerca volvulus*," 1994, pp. 48–49, *Parasite*.

(List continued on next page.)

*Primary Examiner*—Nita Minnifield
(74) *Attorney, Agent, or Firm*—Heska Corporation

(57) ABSTRACT

The present invention includes a method to detect *D. immitis* infection in a host animal using a *D. immitis* Di33 protein to detect anti-*D. immitis* Di33 antibodies in a bodily fluid of the animal. Also included is a method to detect *D. immitis* infection in a host animal using a *D. immitis* anti-Di33 protein to detect Di33 proteins in a bodily fluid of the animal. The present invention also relates to *D. immitis* detection kits that include either a Di33 protein or an anti-Di33 antibody; such kits also include a composition to detect an immunocomplex between the anti-Di33 antibody and *D. immitis* Di33 protein. The present invention also includes Di33 proteins, nucleic acid molecules encoding such proteins, as well as recombinant molecules and recombinant cells comprising such nucleic acid molecules, and anti-Di33 antibodies. Also included are methods to produce such proteins, nucleic acid molecules and antibodies.

17 Claims, 4 Drawing Sheets

OTHER PUBLICATIONS

Martzen, et al., "Primary Structure of the Major Pepsin Inhibitor from the Intestinal Parasitic Nematode *Ascaris suum*," 1990, pp. 7366–7372, *Biochemistry 29*.

Meija, et al., "Expression of an *Onchocerca volvulus* Ov33 homolog in *Dirofilaria immitis*: potential in immunodiagnosis of heartworm infection," 1994, pp. 297–303, *Parasite Immunology 16*.

Ogunrinade, et al., "Preliminary Evaluation of Recombinant *Onchocerca volvulus* Antigens for Serodiagnosis of Onchocerciasis," 1993, pp. 1741–1745, *Journal of Clinical Microbiology 31:7.*.

Soboslay, et al., "Experimental Onchocerciasis in Chimpanzees; Antibody Response and Antigen Recognition after Primary Infection with *Onchocerca volvulus*," 1992, pp. 367–380, *Experimental Parasitology 74*.

Tawill, et al., "Immunodiagnostic studies on *Onchocerca volvulus* and *Mansonella perstans* infections using a recombinant 33 kDa *O. volvulus* protein (Ov33)," 1995, pp. 51–54, *Transactions of the Royal Society of Tropical Medicine and Hygiene 89*.

Willenbücher, et al., "The filarial antigens Av33/Ov33–3 show striking similarities to the major pepsin inhibitor from *Ascaris suum*," 1993, pp. 349–352, *Molecular and Biochemical Parasitology 57*.

* cited by examiner

METHOD TO DETECT *DIROFILARIA IMMITIS* INFECTION

FIELD OF THE INVENTION

The present invention relates to a novel method to detect *D. immitis* infection in animals, particularly in cats. The present invention also includes novel kits to detect *D. immitis* infection as well as methods to purify the detection reagent.

BACKGROUND OF THE INVENTION

The parasitic helminth *D. immitis* has been known for a long time to infect dogs, thereby leading to heartworm. Recently, it has become clear that *D. immitis* also infects other animals, such as cats and ferrets, even though such animals are essentially non-adpated hosts for the infection. That is, the parasitic relationship between *D. immitis* and adapted animals is well adapted, and there are very few clinical signs unless worm burden is very high. In contrast, non-adapted animals, such as cats and ferrets, have a parasitic relationship with *D. immitis* that is not well adapted, resulting in disease and sometimes death for the animal. Heartworm infection in non-adapted animals such as cats is hard to diagnose as there are a variety of clinical signs, some of which are also associated with other diseases. Heartworm disease may be acute or chronic, and can be associated with dyspnea, coughing and vomiting, lethargy, and/or anorexia. Thus, there is a need for an unambiguous method to detect heartworm in animals.

The life cycle of *D. immitis* is complex in all animals it infects, and the organism is difficult to detect, particularly prior to adult worm maturation. Detection is particularly difficult in non-adapted hosts where the worm burden is very low. Cats, for example, harbor, on average, only two to three worms, making detection of *D. immitis*-specific antigens or antibodies difficult.

Sexually mature adults, after mating, produce microfilariae which traverse capillary beds and circulate in the vascular system of the host. One method of demonstrating infection in a dog, for example, is to detect the circulating microfilariae. Another method is to detect *D. immitis* circulating parasite antigens in the blood; these antigens are associated with adult female worms and microfilariae (see, for example, U.S. Pat. No. 4,839,275, issued Jun. 13, 1989, by Weil). In a non-adapted host, however, *D. immitis* infection often results in the maturation of only a single worm, in which case there is no opportunity for reproduction, and eggs and microfilariae are not produced. In addition, the single worm is often a male worm.

If an infected animal is maintained in an insect-free environment, the life cycle of the parasite cannot progress. However, when microfilariae are ingested by the female mosquito during blood feeding on an infected animal, subsequent development of the microfilariae into larvae occurs in the mosquito. The microfilariae go through two larval stages (L1 and L2) and finally become mature third stage larvae (L3) which can then be transmitted back to a host animal through the bite of the mosquito. It is this L3 stage, therefore, that accounts for the initial infection. As early as three days after infection, the L3 molt to the fourth larval (L4) stage, and subsequently to the fifth stage, or immature adults. The immature adults migrate to the heart and pulmonary arteries, where they mature and reproduce, thus producing the microfilariae in the blood. "Occult" infection with heartworm in a host is defined as that wherein no microfilariae can be detected, but the existence of the adult heartworms can be determined by other methods.

Another method to detect heartworm is the use of crude preparations; see, for example, U.S. Pat. No. 4,657,850, issued Apr. 14, 1987, by Grieve. These assays, however, lack desired sensitivity and specificity, particularly to detect infection in a non-adapted host.

Hong et al, 1995, *Proc. Heartworm Symposium*, p. 33, reported the cloning of a gene encoding *D. immitis* antigen DiT33; also see Hong et al, 1994, Abstracts of *Amer. Soc. Trop. Med.Hyg.* Meeting, p191–192. Hong et al., 1995, ibid, also reported that a recombinant fusion protein consisting of DiT33 linked to maltose binding protein could detect *D. immitis* infection in dogs at 11 weeks but did not report any use of the protein to detect *D. immitis* infection in a non-adapted host, such as in a cat or ferret. Previously, several investigators had reported the use of the related protein *Onchocerca volvulus* Ov33 to detect *O. volvulus* or *D. immitis* infection, as well as cloning of the gene encoding *O. volvulus* Ov33; see, for example, Santiago Mejia et al, 1994, *Parasite Immunol* 16, 297–303; Ogunrinade et al, 1993, *J Clin Microbiol* 31, 1741–1745; Lucius et al., 1992, *Trop Med Parasitol* 43, 139–145; Lucius et al, 1988, *J. Exp Med* 168, 1199–1204; Lucius et al, 1988, *J. Exp Med* 167, 1505–1510. A related gene encoding Av33 has been isolated from *Acanthocheilonema viteae*; see, for example, Willenbucher et al, 1993, *Mol. Biochem. Parasitol.* 57, 349–351. Once again, there was no mention of the ability of that protein to detect infection in an animal with a low worm burden prior to adult worm maturation.

There remains a need for an accurate and simple method to detect *D. immitis* infection. Particularly needed is a method that would detect *D. immitis* infection prior to maturation of larvae into adult heartworms, but would not detect early infections that never develop into full-term infections, i.e., infections that the host immune response is able to prevent from developing into mature worms.

SUMMARY OF THE INVENTION

The present invention includes detection methods and kits that detect *D. immitis* infection prior to maturation of larvae into adult heartworms, but do not detect early infections that do not develop into full-term infections (i.e., infections that do not lead to mature heartworm development).

The present invention includes a method to detect *D. immitis* in a non-adapted host that includes the steps of: (a) contacting a bodily fluid collected from the host with a formulation comprising an isolated *D. immitis* Di33 protein under conditions sufficient to form an immunocomplex between Di33 protein and anti-Di33 antibodies; and (b) measuring immunocomplex formation between the Di33 protein and anti-Di33 antibodies, if any, in the fluid, wherein the presence of such an immunocomplex indicates that the host is or has recently been infected with *D. immitis.*

The present invention also includes a method to detect *D. immitis* in a host animal, which includes the steps of: (a) contacting a bodily fluid collected from the animal with a formulation comprising an isolated *D. immitis* Di33 protein under conditions sufficient to form an immunocomplex between Di33 protein and anti-Di33 IgE antibodies; and (b) immunocomplex formation between the Di33 protein and anti-Di33 IgE antibodies, if any, in the fluid, wherein the presence of such an immunocomplex indicates that the animal is or has recently been infected with *D. immitis.*

Also included in the present invention is a method to detect *D. immitis* infection in a non-adapted host within 10 weeks of infection, the method comprising detecting anti-Di33 antibodies in a bodily fluid collected from the host.

The present invention also includes a method to detect *D. immitis* in a non-adapted host, that includes the steps of: (a) contacting a bodily fluid collected from the host with a formulation comprising an isolated anti-Di33 antibody under conditions sufficient to form an immunocomplex between the anti-Di33 antibody and *D. immitis* Di33 protein; and (b) measuring immunocomplex formation between the anti-Di33 antibody and *D. immitis* Di33 protein, if any, in the fluid, wherein the presence of such an immunocomplex indicates that the host is or recently has been infected with *D. immitis.*

One embodiment of the present invention is a kit to detect *D. immitis* infection that includes an isolated *D. immitis* Di33 protein and a composition to detect antibodies capable of forming an immunocomplex with the Di33 protein. Another embodiment is a kit to detect *D. immitis* infection that includes an isolated anti-Di33 antibody and a composition to detect an immunocomplex between the anti-Di33 antibody and *D. immitis* Di33 protein.

The present invention also includes Di33 proteins, nucleic acid molecules encoding such proteins, as well as recombinant molecules and recombinant cells comprising such nucleic acid molecules, and anti-Di33 antibodies. Examples of Di33 proteins include, but are not limited to, PHIS-$PDi33_{234}$ and $PDi33_{217}$. Examples of Di33 nucleic acid molecules include, but are not limited to, $nDi33_{346}$, $nDi33_{750}$, $nDi33_{702}$, $nDi33_{708}$, and $nDi33_{651}$. Also included are methods to produce Di33 nucleic acid molecules, Di33 nucleic acid molecule-containing recombinant molecules, Di33 nucleic acid molecule-containing recombinant cells, Di33 proteins and anti-Di33 antibodies.

One embodiment of the present invention is a method to produce an isolated *D. immitis* Di33 protein that includes the steps of (a) culturing a bacterium transformed with a *D. immitis* Di33 nucleic acid molecule to produce a *D. immitis* Di33 protein-containing culture; (b) recovering insoluble material comprising the Di33 protein from the culture; and (c) purifying the Di33 protein from the insoluble material. Also included is a method for purifying a *D. immitis* Di33 protein comprising recovering Di33 protein from cation exchange chromatography of disrupted insoluble material obtained from a culture of *D. immitis* Di33 protein-producing recombinant cells.

DETAILED DESCRIPTION OF THE INVENTION

Figure 1:
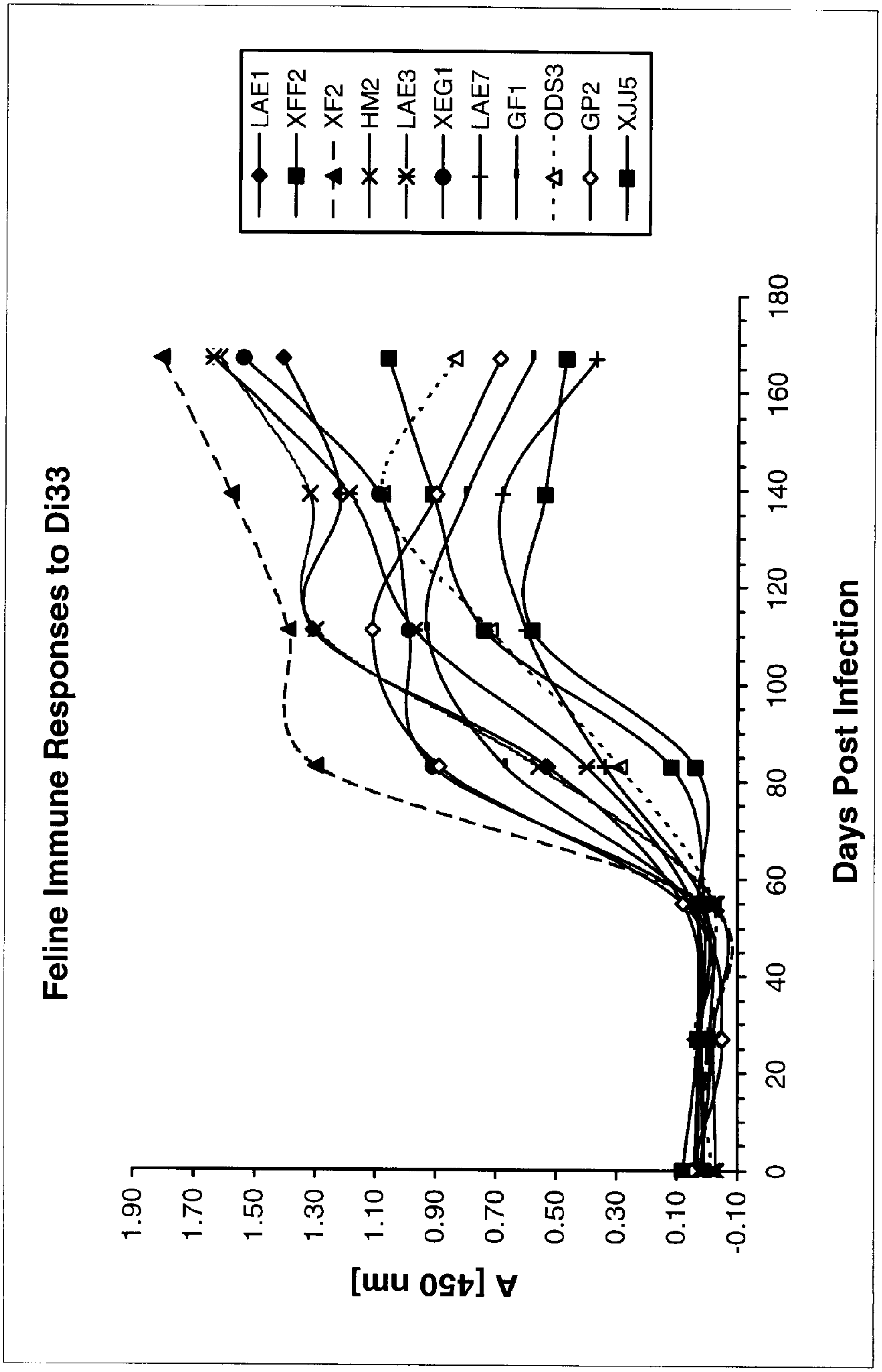
FIG. 1 depicts ELISA results using a heartworm detection reagent of the present invention to detect anti-Di33 IgG antibodies in *D. immitis*-infected cats.

The present invention relates to the surprising discovery that *D. immitis* Di33 protein-based detection (e.g., diagnostic, screening) methods and kits can detect *D. immitis* infection in a non-adapted host (i.e., an animal susceptible to heartworm infection in which *D. immitis* does not establish a parasitic relationship) at the time that the *D. immitis* larvae are maturing from L4 to L5, even though the worm burden in such a host is very low. As such, *D. immitis* detection methods and kits of the present invention are able to detect *D. immitis* in a non-adapted host prior to maturation of the *D. immitis* into an adult heartworm. Thus, unlike assays based solely on detection of reagents linked to egg-laying, methods and kits of the present invention detect *D. immitis* infection before adult heartworms are sexually active; heartworms usually become reproductively active at about 6.5 months post infection. *D. immitis* detection methods and kits of the present invention can detect *D. immitis* in a non-adapted host at least about ten weeks, and in some cases as early as about eight weeks post (i.e., following) infection of the host with *D. immitis. D. immitis* infection can also be detected in non-adapted hosts harboring adult heartworms. As such, *D. immitis* infection can be detected at any time from about 8 to 10 weeks post infection through the adult life stage of the heartworm, which in cats, for example, is about 2 to 3 years. As such, *D. immitis* can be detected at about 12 weeks, 16 weeks, 20 weeks, and 24 weeks (e.g., about 6 months) following infection, as well as at any intermittent or later times. *D. immitis* infections of less than about 4 to about 6 weeks, however, are not typically detected using Di33 protein. Detection methods and kits of the present invention are particularly usefull in that they can detect infection in a non-adapted host harboring (i.e., maintaining, having for a sustained time, infected with) only a single worm. Moreover, detection methods and kits of the present invention can detect an infection resulting in a single male worm or in a single female worm. It is to be noted, of course, that the *D. immitis* Di33-based methods and kits of the present invention can also detect larger worm burden, including, but not limited to, 2, 3, 4 or 5 worms. Therefore, the methods and kits of the present invention can detect *D. immitis* infection in any infected non-adapted host, except for very early-stage infections that are likely to resolve themselves or that may be treated by monthly anti-helminth drug applications, and thus do not develop into full-term infections (i.e., infections that do not lead to mature heartworm development). Detection methods of the present invention are not only very sensitive, but also are specific for *D. immitis* infection.

Another discovery of the present invention is that *D. immitis* infection stimulates the production of anti-*D. immitis* Di33 immunoglobulin E antibodies (anti-Di33 IgE antibodies) as well as of other isotypes of anti-*D. immitis* Di33 antibodies, such as anti-*D. immitis* Di33 immunoglobulin G antibodies (anti-Di33 IgG antibodies). Thus, the present invention also includes *D. immitis* detection methods and kits based on detection of anti-Di33 IgE antibodies, as well as methods and kits based on detection of other isotypes of anti-Di33 antibodies, such as anti-Di33 IgG antibodies. While not being bound by theory, it is believed that anti-Di33 IgE-based methods and kits may have increased specificity compared to anti-Di33 IgG-based methods and kits, whereas anti-Di33 IgG-based methods and kits are more sensitive than anti-Di33 IgE-based methods and kits.

The present invention includes a method to detect *D. immitis* (i.e., heartworm infection) in a non-adapted host using an isolated *D. immitis* Di33 protein to detect any anti-Di33 antibodies present in a bodily fluid collected from such a host. The present invention also includes a method to detect *D. immitis* in any animal susceptible to *D. immitis* infection using an isolated *D. immitis* Di33 protein to detect anti-Di33 IgE antibodies. Another embodiment is the use of anti-Di33 antibodies to detect *D. immitis* infection. Also included in the present invention are kits to detect *D. immitis* infection based on such methods as well recombinant molecules and recombinant cells to produce *D. immitis* Di33 proteins and methods to purify such proteins.

It is to be noted that the term "a" entity or "an" entity refers to one or more of that entity; for example, a protein refers to one or more proteins or at least one protein. As such, the terms "a" (or "an" ), "one or more" and "at least one" can be used interchangeably herein. It is also to be noted that the terms "comprising", "including", and "having" can be used interchangeably.

According to the present invention, an isolated, or biologically pure, *D. immitis* Di33 protein, is a protein that has been removed from its natural milieu. As such, "isolated" and "biologically pure" do not necessarily reflect the extent to which the protein has been purified. An isolated *D. immitis* Di33 protein of the present invention can be obtained from its natural source (i.e., from *D. immitis*), can be produced using recombinant DNA technology or can be produced by chemical synthesis.

As used herein, an isolated *D. immitis* Di33 protein (also referred to herein as a Di33 protein, or a *D. immitis* protein of about 33 kilodaltons (kd)) can be a full-length protein or any homolog of such a protein. An isolated Di33 protein of the present invention, including a homolog, can be identified in a straight-forward manner by the Di33 protein's ability to form an immunocomplex with an anti-*D. immitis* Di33 antibody, also referred to herein as an anti-Di33 antibody; anti-Di33 antibodies are described in more detail elsewhere herein. Examples of Di33 homologs include Di33 proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homolog includes at least one epitope capable of forming an immunocomplex with an anti-Di33 antibody.

Di33 protein homologs can be the result of natural allelic variation or natural mutation. Di33 homologs of the present invention can also be produced using techniques known in the art including, but not limited to, direct modifications to the protein or modifications to the gene encoding the protein using, for example, classic or recombinant DNA techniques to effect random or targeted mutagenesis. The nucleic acid sequence of the coding strand of a cDNA encoding an apparent full-length Di33 protein of the present invention is represented herein as SEQ ID NO:2. The double-stranded nucleic acid molecule including both the coding strand having SEQ ID NO:2 and the complementary non-coding strand ( the nucleic acid sequence of which can be readily determined by one skilled in the art) is referred to herein as Di33 nucleic acid molecule $nDi33_{750}$. Translation of SEQ ID NO:2 suggests that nucleic acid molecule $nDi33_{750}$ encodes a full-length *D. immitis* Di33 protein of about 234 amino acids, referred to herein as $PDi33_{234}$, represented by SEQ ID NO:3, assuming an open reading frame having an initiation (start) codon spanning from about nucleotide 24 through about nucleotide 26 of SEQ ID NO:2 and a termination (stop) codon spanning from about nucleotide 726 through about nucleotide 728 of SEQ ID NO:2. The coding region encoding $PDi33_{234}$, excluding the stop codon, is represented by nucleic acid molecule $nDi33_{702}$, having a coding strand with the nucleic acid sequence represented herein as SEQ ID NO:4. SEQ ID NO:4 appears to encode a signal peptide of about 17 amino acids as well as an apparent mature protein of about 217 amino acids, denoted herein as $PDi33_{217}$, the amino acid sequence of which is represented herein as SEQ ID NO:7. The nucleic acid molecule encoding the apparent mature protein is referred to as $nDi33_{651}$, the nucleic acid sequence of the coding strand of which is denoted herein as SEQ ID NO:6. Knowledge of these nucleic acid and amino acid sequences allows one skilled in the art to make modifications to the respective nucleic acid molecules and proteins to, for example, develop a Di33 protein with increased solubility and/or a truncated protein (e.g., a peptide) capable of detecting *D. immitis* Di33 infection. For example, modifications to $PHIS\text{-}PDi33_{234}$ (the production of which is described in the Examples) likely to yield a more soluble protein include, but are not limited to, deletion of the putative signal sequence and/or protein iodoacetimidation.

The present invention also includes the use of Di33 mimetopes to detect *D. immitis* infection. In accordance with the present invention, a "mimetope" refers to any compound that is able to mimic the ability of a Di33 protein to bind to an anti-Di33 antibody. A mimetope can be a peptide that has been modified to decrease its susceptibility to degradation but that still retains antibody-binding activity. Other examples of mimetopes include, but are not limited to, carbohydrate-based compounds, lipid-based compounds, nucleic acid-based compounds, natural organic compounds, synthetically derived organic compounds, anti-idiotypic antibodies and/or catalytic antibodies, or fragments thereof. A mimetope can be obtained by, for example, screening libraries of synthetic compounds for compounds capable of binding to anti-Di33 antibodies. A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modeling. The predicted mimetope structures can then be produced by, for example, chemical synthesis, recombinant DNA technology, or by isolating a mimetope from a natural source.

Also included in the present invention are anti-*D. immitis* Di33 antibodies, also referred to as anti-Di33 antibodies. Such antibodies are able to selectively bind to a Di33 protein of the present invention. As used herein, the term "selectively binds to" refers to the ability of such an antibody to preferentially bind to a Di33 protein of the present invention, without being able to substantially bind to other proteins. Binding can be measured using a variety of methods known to those skilled in the art including immunoblot assays, immunoprecipitation assays, enzyme immunoassays (e.g., ELISA), radioimmunoassays, immunofluorescent antibody assays and immunoelectron microscopy; see, for example, Sambrook et al., 1989, *Molecular Cloning: A Laboratory Manual*, Cold Spring Harbor,Labs Press. Antibodies of the present invention can be either polyclonal or monoclonal antibodies. Antibodies of the present invention include functional equivalents such as antibody fragments, genetically-engineered antibodies, including single chain antibodies, and antibody mimetopes that are capable of selectively binding to at least one of the epitopes of a Di33 protein or Di33 mimetope used to obtain the antibodies. Preferably, an antibody of the present invention has a single site binding affinity of from about $10^3\ M^{-1}$ to about $10^{12}\ M^{-1}$ for a Di33 protein of the present invention. A preferred method to produce antibodies of the present invention includes administering to an animal an effective amount of a Di33 protein or mimetope thereof to produce the antibody and recovering the antibodies. Antibodies raised against defined products or mimetopes can be advantageous because such antibodies are not substantially contaminated with antibodies against other substances that might otherwise cause interference in a diagnostic assay or side effects if used in a therapeutic composition.

One embodiment of the present invention is a method to detect *D. immitis* infection in a non-adapted host which includes the steps of: (a) contacting a bodily fluid collected from such a host with a formulation including an isolated *D. immitis* Di33 protein under conditions sufficient to form an immunocomplex between Di33 protein and anti-Di33 antibodies; and (b) measuring immunocomplex formation between the Di33 protein and anti-Di33 antibodies, if any, in the bodily fluid. Presence of such a Di33 protein:anti-Di33 antibody (Di33:anti-Di33) immunocomplex indicates that the host is infected or recently has been infected (e.g., recently infected followed by chemotherapy treatment in a time frame that anti-Di33 antibodies are still present) with *D. immitis*. As used herein, a non-adapted host refers to any animal susceptible to heartworm infection but in which *D. immitis* does not establish a well- adapted parasitic relationship. Examples of non-adapted hosts include, but are not limited to cats, ferrets, and other members of the family Mustelidae. As used herein, a cat refers to any member of the cat family (i.e., Felidae), including domestic cats, wild cats and zoo cats. Examples of cats include, but are limited to, domestic cats, lions, tigers, leopards, panthers, cougars, bobcats, lynx, jaguars, cheetahs, and servals. A preferred cat to test for *D. immitis* infection is a domestic cat.

A bodily fluid refers to any fluid that can be collected (i.e., obtained) from an animal, examples of which include, but are not limited to, blood, serum, plasma, urine, tears, saliva, lymph, nasal secretions, and feces.

A formulation comprising an isolated *D. immitis* Di33 protein refers to a composition that at least includes Di33 protein. Such a formulation can also, but need not, include, for example, a buffer in which the Di33 protein is solubilized, and/or a carrier. Suitable buffers and carriers are known to those skilled in the art. Examples of suitable buffers include any buffer in which a protein or antibody can function to selectively bind to its partner, such as, but not limited to, phosphate buffered saline, water, saline, phosphate buffer, bicarbonate buffer, HEPES buffer (N-2-hydroxyethylpiperazine-N'-2-ethanesulfonic acid buffered saline), TES buffer (Tris-EDTA buffered saline), Tris buffer and TAE buffer (Tris-acetate-EDTA). Examples of carriers include, but are not limited to, polymeric matrices, toxoids, and serum albumins, such as bovine serum albumin. Carriers can be in admixture with the Di33 protein or conjugated (i.e., attached) to the Di33 protein in such a manner as to not substantially interfere with the ability of the Di33 protein to selectively bind to anti-Di33 antibodies. Formulations of the present invention can also include not only a Di33 protein or an anti-Di33 antibody but also one or more additional *D. immitis* antigens or antibodies useful in detecting *D. immitis* infection. Examples of such antigens and antibodies include, but are not limited to, *D. immitis* P22U (see PCT Publication No. WO 94/15593, published Jul. 21, 1994, by Grieve et al.), *D. immitis* P39 (see WO 94/15593, ibid.), *D. immitis* Gp29 (see PCT Publication No. WO 95/24198, published Sep. 14, 1995, by Tripp et al.), *D. immitis* cystatin, *D. immitis* ladder protein, *D. immitis* circulating antigens (see, for example, U.S. Pat. No. 4,839,275, ibid., and antibodies to any of those antigens.

As used herein, the term "contacting" refers to combining or mixing, in this case a bodily fluid with an isolated Di33 protein. Formation of an immunocomplex between a Di33 protein and an anti-Di33 antibody refers to the ability of the Di33 protein to selectively bind to the anti-Di33 antibody in order to form a stable complex that can be measured (i.e., detected). As used herein, the term selectively binds to an anti-Di33 antibody refers to the ability of a Di33 protein of the present invention to preferentially bind to anti-Di33 antibodies, without being able to substantially bind to other antibodies. Binding between a Di33 protein and an anti-Di33 antibody is effected under conditions sufficient to form an immunocomplex; such conditions (e.g., appropriate concentrations, buffers, temperatures, reaction times) as well as methods to optimize such conditions are known to those skilled in the art, and examples are disclosed herein. Examples of immunocomplex formation conditions are also disclosed, for example, in Sambrook et al., ibid., the reference Sambrook et al., ibid., is incorporated by reference herein in its entirety.

As used herein, the term "measuring immunocomplex formation" refers to determining if any immunocomplex is formed, i.e., assaying for the presence of an immunocomplex. If immunocomplexes are formed, the amount of immunocomplexes formed can, but need not be, determined. The phrase "anti-Di33 antibodies, if any, in the bodily fluid" refers to the possibility that such antibodies may or may not be present depending on whether the animal is infected or whether infection is very early or has been resolved prior to anti-Di33 antibody formation. Immunocomplex formation, or selective binding, between Di33 and any anti-Di33 antibody in the bodily fluid can be measured (i.e., detected, determined) using a variety of methods standard in the art (see, for example, Sambrook et al. ibid.), examples of which are disclosed herein.

In accordance with the present invention, a Di33 protein can form an immunocomplex with any anti-Di33 antibody in a bodily fluid, including IgG, IgE, IgM and IgA antibodies. Preferred antibodies to detect include IgG, IgE and IgM antibodies, with IgG and IgE antibodies being even more preferred. In one embodiment in which anti-Di33 IgE antibodies are being detected, the collected bodily fluid is pretreated to remove at least some of the other isotypes of immunoglobulin and/or other proteins, such as albumin, present in the fluid. Such removal can include, but is not limited to, contacting the bodily fluid with a material, such a Protein G, to remove IgG antibodies and/or affinity purifying the IgE antibodies from other components of the body fluid by exposing the fluid to, for example, Concanavalin A.

An immunocomplex can be measured in a variety of ways including, but not limited to use of one or more of the following assays: an enzyme-linked immunoassay, a radioimmunoassay, a fluorescence immunoassay, a lateral flow assay, an agglutination assay, a particulate-based assay (e.g., using particulates such as, but not limited to, magnetic particles or plastic polymers, such as latex or polystyrene beads), an immunoprecipitation assay, and an immunoblotting assay (e.g., a Western blot). Such assays are well known to those skilled in the art. Assays can be used to give qualitative or quantitative results depending on how they are used. Some assays, such as agglutination, particulate separation, and immunoprecipitation, can be observed visually (e.g., either by eye or by a machines, such as a densitometer or spectrophotometer) without the need for a detectable marker. In other assays, conjugation of a detectable marker to the Di33 protein or to a composition that selectively binds to the antibody being detected (described in more detail below) aids in measuring immunocomplex formation. Detectable markers are conjugated to either the Di33 protein or the composition in such a manner as not to block the ability of the Di33 protein or composition to bind to the antibodies being detected. Examples of detectable markers include, but are not limited to, an enzyme label (e.g., horse radish peroxidase, alkaline phosphatase), a radioactive label, a fluorescent label, a chemiluminescent label, a chromophoric label (e.g., a colorimetric label), and a ligand (e.g., biotin, avidin, streptavidin, and related compounds).

In one embodiment, an immunocomplex is measured by contacting the Di33 protein-contacted bodily fluid (i.e., the result of contacting a bodily fluid with a Di33 protein) with a composition that selectively binds to one of the following antibody isotypes: an IgG antibody, an IgE antibody, an IgM antibody or an IgA antibody. Examples of such a composition include, but are not limited to, a secondary antibody that is an anti-isotype antibody (e.g., an antibody that selectively binds to the constant region of the host antibody that bound to Di33, such as an anti-feline immunoglobulin antibody), an antibody-binding bacterial surface protein (e.g., Protein A or Protein G), an antibody-binding cell (e.g., a B cell, T cell, or macrophage), an antibody-binding eukaryotic cell surface protein (e.g., an Fc receptor), and an antibody-binding complement protein. Preferred compositions include an anti-IgG antibody, an anti-IgE antibody, an anti-IgM antibody, an anti-IgA antibody, an $Fc_\gamma$ receptor molecule, an $Fc_\epsilon$ receptor molecule, an $Fc_\mu$ receptor molecule, and an $Fc_\alpha$ receptor molecule. As used herein an Fc receptor molecule includes not only a complete Fc receptor but also any subunit or portion thereof that is capable of selectively binding to an antibody heavy chain constant region. For example, an $Fc_\epsilon$ receptor molecule can be a complete $Fc_\epsilon$ receptor (which can either be associated with a cell or isolated from a cell), an $Fc_\epsilon$ receptor $\alpha$ chain, or any portion of an $Fc_\epsilon$ receptor $\alpha$ chain that can selectively bind to an IgE antibody heavy chain constant region. It is within the scope of the present invention that the amount of antibody from the bodily fluid bound to a Di33 protein can be determined using one or more layers and/or types of secondary antibodies or other binding compounds. For example, an untagged secondary antibody can be bound to an anti-Di33 antibody from the bodily fluid and the untagged secondary antibody can then be bound by a tagged tertiary antibody.

In one embodiment an immunocomplex can be formed and measured in solution. In another embodiment, either the Di33 protein or the composition being used to bind to the anti-Di33 antibody can be immobilized on (e.g., coated onto) a substrate. Immobilization techniques are known to those skilled in the art. Suitable substrate materials on which to immobilize a Di33 protein or a composition include, but are not limited to, plastic, glass, gel, celluloid, paper and particulate materials such as latex, polystyrene, nylon, nitrocellulose, agarose, PVDF (poly-vinylidene-fluoride), and magnetic resin. Suitable substrates include, but are not limited to, a well (e.g., microtiter dish well), a plate, a dipstick, a bead, a lateral flow apparatus, a membrane, a filter, a tube, a dish, a celluloid-type matrix, a magnetic particle, and other particulates. In one embodiment, a substrate, such as a particulate, can include a detectable marker.

A preferred method to detect *D. immitis* infection is an immunosorbent assay. In one embodiment, a Di33 protein is immobilized on a substrate, such as a microtiter dish well or a dipstick. A bodily fluid collected from an animal is applied to the substrate and incubated under conditions sufficient to allow for immunocomplex formation. Excess fluid, if any, is removed and a composition that can selectively bind to an anti-Di33 antibody bound to the Di33 protein, the composition being conjugated to a detectable marker (preferably to an enzyme label, to a colorimetric label, to a fluorescent label, to a radioisotope, or to a ligand such as of the biotin or avidin family), is added to the substrate and incubated to allow formation of a complex between the composition and the immunocomplex. Excess composition is removed, a developing agent is added if required, and the substrate is submitted to a detection device for analysis. Alternatively, an antibody-binding composition as described above is immobilized on a substrate, and bodily fluid is incubated with the substrate to form an immunocomplex. Immunocomplex detection can then be accomplished by applying a marker-conjugated Di33 protein to the immunocomplex.

Another preferred method to detect *D. immitis* infection is a lateral flow assay, examples of which are disclosed in U.S. Pat. No. 5,424,193, issued Jun. 13, 1995, by Pronovost et al.; U.S. Pat. No. 5,415,994, issued May 16, 1995, by Imrich et al; WO 94/29696, published Dec. 22, 1994, by Miller et al.; and WO 94/01775, published Jan. 20, 1994, by Pawlak et al.; each of these patent publications is incorporated by reference herein in its entirety. In one embodiment, a bodily fluid sample is placed in a lateral flow apparatus that includes the following components: (a) a support structure defining a flow path; (b) a labeling reagent comprising a bead conjugated to a Di33 protein, the labeling reagent being impregnated within the support structure in a labeling zone; and (c) a capture reagent comprising an antibody-binding composition. The capture reagent is located downstream of the labeling reagent within a capture zone fluidly connected to the labeling zone in such a manner that the labeling reagent can flow from the labeling zone into the capture zone. The support structure comprises a material that does not impede the flow of the beads from the labeling zone to the capture zone. Examples of such a material include, but are not limited to, nitrocellulose and PVDF. The support structure defines a flow path that is lateral and is divided into zones, namely a labeling zone and a capture zone. The apparatus can further comprise a sample receiving zone located along the flow path, more preferably upstream of the labeling reagent. The flow path in the support structure is created by contacting a portion of the support structure downstream of the capture zone, preferably at the end of the flow path, to an absorbent capable of absorbing excess liquid from the labeling and capture zones.

In this embodiment, the bodily fluid is applied to the sample receiving zone which includes a portion of the support structure. The labeling zone receives the sample from the sample receiving zone which is directed downstream by the flow path. The labeling zone comprises the labeling reagent that binds to anti-Di33 antibodies. A preferred labeling reagent is a Di33 protein conjugated, either directly or through a linker, to a plastic bead substrate, such as a to latex bead. The substrate also includes a detectable marker, preferably a calorimetric marker. Typically, the labeling reagent is impregnated to the support structure by drying or lyophilization. The sample structure also comprises a capture zone downstream of the labeling zone. The capture zone receives labeling reagent from the labeling zone which is directed downstream by the flow path. The capture zone contains the capture reagent, in this case an antibody-binding composition, as disclosed above, that immobilizes the immunocomplex-containing labeling reagent (i.e., anti-Di33 complexed to the Di33 protein portion of the labeling reagent) in the capture zone. The capture reagent is preferably fixed to the support structure by drying or lyophilizing. The labeling reagent accumulates in the capture zone and the accumulation is assessed visibly or by an optical detection device.

In another embodiment, a lateral flow apparatus used to detect *D. immitis* infection includes: (a) a support structure defining a flow path; (b) a labeling reagent comprising an antibody-binding composition as described above, the labeling reagent impregnated within the support structure in a labeling zone; and (c) a capture reagent comprising a Di33 protein, the capture reagent being located downstream of the labeling reagent within a capture zone fluidly connected to the labeling zone in such a manner that the labeling reagent can flow from the labeling zone into the capture zone. The apparatus preferably also includes a sample receiving zone located along the flow path, preferably upstream of the labeling reagent. The apparatus preferably also includes an absorbent located at the end of the flow path.

Another embodiment of the present invention is a method to detect *D. immitis* in a host animal. The method includes the steps of: (a) contacting a bodily fluid collected from the animal with a formulation that includes an isolated *D. immitis* Di33 protein under conditions sufficient to form an immunocomplex between Di33 protein and anti-Di33 IgE antibodies; and (b) measuring immunocomplex formation between the Di33 protein and anti-Di33 IgE antibodies, if any, in the fluid. Presence of such a Di33 protein:anti-Di33 IgE antibody immunocomplex indicates that the animal is or has recently been infected with *D. immitis*. As used herein a host animal refers to any animal that is susceptible to *D. immitis* infection and, as such, includes either adapted or non-adapted hosts (i.e., animals with which *D. immitis* either does or does not, respectively, establish a parasitic relationship). Examples of host animals include any mammal susceptible to *D. immitis* infection, including, but are limited to, cats, dogs, ferrets as well as other members of the family Mustelidae, sea lions as well as other sea mammals of the order Pinnipedia, and humans as well as other prinmates. It is to be noted that the term dog refers to any member of the family Canidae, including, but not limited to, domestic dogs, wild dogs, foxes, wolves, jackals, and coyotes. As noted above, a cat can be any member of the family Felidae. Preferred animals to test include domestic cats, domestic dogs, and ferrets. Immunocomplex formation and measurement methods are as disclosed above, except that antibody-binding compositions are limited to those compositions that bind to the heavy chain constant region of IgE, such as, but not limited to, anti-IgE antibodies and $Fc_\epsilon$ receptor molecules, such as a complete $Fc_\epsilon$ receptor, an $Fc_\epsilon$ receptor $\alpha$ chain, or a portion of the $Fc_\epsilon$ receptor a chain that binds to the IgE heavy chain constant region. Not only can anti-Di33 IgE antibodies by detected using in vitro techniques such as those disclosed above, but anti-Di33 IgE antibodies can also be detected using in vivo techniques, such as skin testing. In vivo methods to detect IgE antibodies are known in the art; examples of such methods are disclosed in PCT Patent Publication No. WO 96/11271, published Apr. 18, 1996, by Frank et al.; this publication is incorporated by reference herein in its entirety.

Yet another embodiment of the present invention is a method to detect *D. immitis* in a non-adapted host that includes the steps of: (a) contacting a bodily fluid collected from the host with a formulation comprising an isolated anti-Di33 antibody under conditions sufficient to form an immunocomplex between said anti-Di33 antibody and *D. immitis* Di33 protein; and (b) measuring immunocomplex formation between the anti-Di33 antibody and *D. immitis* Di33 protein, if any, in the fluid. Presence of such an immunocomplex indicates that the host is or recently has been infected with *D. immitis*. Anti-Di33 antibodies of the present invention, as well as methods to produce same, are disclosed herein. Methods to form immunocomplexes and to measure immunocomplex formation are similar to those disclosed elsewhere herein, except that in this case it is natural Di33 protein being detected using isolated antibodies. Those skilled in the art can make adjustments to the disclosed methods to practice this embodiment.

The present invention also includes kits to detect *D. immitis* infection based on each of the disclosed detection methods. One embodiment is a kit to detect *D. immitis* infection that includes an isolated *D. immitis* Di33 protein and a composition to detect antibodies capable of forming an immunocomplex with the Di33 protein. Another embodiment is a kit that includes an isolated anti-Di33 antibody and a composition to detect an immunocomplex between the anti-Di33 antibody and a *D. immitis* Di33 protein. For both embodiments, examples of such compositions are disclosed herein, such compositions being able to detect IgG, IgE, IgM or IgA antibodies. Preferred kits include those in which the Di33 protein or anti-Di33 antibody, respectively is immobilized to a substrate. A kit can also contain two or more diagnostic reagents for *D. immitis* infection, one being an isolated Di33 protein or an isolated anti-Di33 antibody, the other(s) being additional isolated *D. immitis* antigens and/or antibodies as disclosed herein. Also preferred are kits in which the antibody-binding composition is immobilized to a substrate. Particularly preferred are kits used in an immunosorbent assay or a lateral flow assay format.

The present invention also includes a method to produce Di33 proteins of the present invention. A Di33 protein of the present invention can be isolated from *D. immitis*, can be produced recombinantly, or can be chemically synthesized. A preferred method to produce a Di33 protein is recombinant Di33 protein production.

One embodiment of the present invention is a method to produce a Di33 protein that includes the steps of: (a) culturing a recombinant cell that expresses a Di33 protein to produce the protein; and (b) recovering the protein. As such, the present invention also includes isolated Di33 nucleic acid molecules that encode Di33 proteins of the present invention as well as recombinant molecules and recombinant cells that include such Di33 nucleic acid molecules. An isolated Di33 nucleic acid molecule refers to a nucleic acid molecule that has been removed from its natural milieu. As such, "isolated" and "biologically pure" do not necessarily reflect the extent to which the nucleic acid molecule has been purified. An isolated *D. immitis* Di33 nucleic acid molecule of the present invention can be obtained from its natural source (i.e., from *D. immitis*), can be produced using recombinant DNA technology or can be produced by chemical synthesis. An isolated *D. immitis* Di33 nucleic acid molecule is any molecule that encodes a Di33 protein of the present invention. Examples of Di33 nucleic acid molecules include, but are not limited to, $nDi33_{346}$, $nDi33_{750}$, $nDi33_{702}$, $nDi33_{708}$, and $nDi33_{651}$, the production of which is disclosed in the Examples.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of Di33 nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, helminth or other parasite, insect and mammalian cells and more preferably in bacteria.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth or other parasite, insect and mammalian cells. More preferred transcription control sequences include those that function in bacteria, such as, but not limited to, tac, lac, trp, trc, oxy-pro, omp/lpp, rmB, bacteriophage lambda(such as lambda PL and lambda PR and fusions that include such promoters), bacteriophage T7, T7lac, bacteriophage T3, bacteriophage SP6, bacteriophage SP01, and antibiotic resistance gene transcription control sequences.

Suitable and preferred nucleic acid molecules to include in recombinant vectors of the present invention are as disclosed herein. Preferred nucleic acid molecules to include in recombinant vectors, and particularly in recombinant molecules, include $nDi33_{346}$, $nDi33_{750}$, $nDi33_{702}$, $nDi33_{708}$, and $nDi33_{651}$. Particularly preferred recombinant molecules of the present invention include $p\lambda PR\text{-}nDi33_{708}$ and $p\lambda PR\text{-}nDi33_{651}$, the production of which are described in the Examples section.

Recombinant molecules of the present invention may also (a) contain secretory signals (i.e., signal segment nucleic acid sequences) to enable an expressed parasitic helminth protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Suitable fusion segments for use with the present invention include, but are not limited to, segments that can: enhance a protein's stability and/or assist purification of a Di33 protein (e.g., by affinity chromatography). A suitable fusion segment can be a domain of any size that has the desired function (e.g., imparts increased stability and/or simplifies purification of a protein). Fusion segments can be joined to amino and/or carboxyl termini of the Di33 domain of the protein and can be susceptible to cleavage in order to enable straight-forward recovery of a Di33 protein. Fusion proteins are preferably produced by culturing a recombinant cell transformed with a fusion nucleic acid molecule that encodes a protein including the fusion segment attached to either the carboxyl and/or amino terminal end of a domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, other domains that can be purified using compounds that bind to the domain, such as monoclonal antibodies). A more preferred fusion segment is a metal binding domain. Examples of particularly preferred fusion proteins of the present invention include $PHIS\text{-}PDi33_{234}$, production of which is disclosed herein.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection; adsorption, and protoplast fusion. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include Di33 nucleic acid molecules disclosed herein. Particularly preferred nucleic acid molecules with which to transform a cell include $nDi33_{346}$, $nDi33_{750}$, $nDi33_{702}$, $nDi33_{708}$, and $nDi33_{651}$.

Suitable host cells to transform include any cell that can be transformed with a nucleic acid molecule of the present invention. Host cells can be either untransformed cells or cells that are already transformed with at least one nucleic acid molecule. Host cells of the present invention can be any cell capable of producing at least one protein of the present invention, and include bacterial, fungal (including yeast), parasite (including helminth, protozoa and ectoparasite), other insect, other animal and plant cells. Preferred host cells include bacterial cells, with Salmonella, Escherichia, and Bacillus being more preferred and *E. coli* being particularly preferred. A recombinant cell is preferably produced by transforming a host cell with a recombinant molecule comprising a Di33 nucleic acid molecule of the present invention operatively linked to an expression vector containing a transcription control sequence. The phrase operatively linked refers to insertion of a nucleic acid molecule into an expression vector in a manner such that the molecule is able to be expressed when transformed into a host cell. Particularly preferred recombinant molecules include $p\lambda PR\text{-}nDi33_{708}$ and $p\lambda PR\text{-}nDi33_{651}$. Particularly preferred recombinant cells include *E. coli*:pλPR-nDi33$_{708}$ and *E. coli*:pλPR-nDi33$_{65}$. Details regarding the production of these recombinant cells are disclosed herein.

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated Di33 proteins of the present invention, including, but not limited to PHIS-PDi33$_{234}$ and PDi33$_{217}$, can be produced in a variety of ways, including production and recovery of natural proteins, production and recovery. of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective, medium refers to any medium in which a cell is cultured to produce a Di33 protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, Concanavalin A chromatography, chromatofocusing and differential solubilization. Proteins of the present invention are preferably retrieved in "substantially pure" form. As used herein, "substantially pure" refers to a purity that allows for the effective use of the protein as a detection reagent.

One embodiment of the present invention is a method to purify a Di33 protein that includes the steps of: (a) culturing a bacterium transformed with a *D. immitis* Di33 nucleic acid molecule to produce a *D. immitis* Di33 protein-containing culture; (b) recovering insoluble material (believed to be refractile bodies) that include Di33 protein from the culture; and (c) purifying the Di33 protein from the insoluble material. The purifying step preferably includes the steps of (a) disrupting the insoluble material to form a solution comprising Di33 protein; (b) submitting the solution to cation exchange chromatography; and (c) recovering the Di33 protein. Use of such a method results in a protein that is at least about 80% pure and preferably about 90% pure. If the recovered protein is then submitted to hydrophobic interaction chromatography and that protein recovered, the resultant protein is at least about 95% pure and preferably at least about 99% pure. The present invention also includes proteins purified according to these methods. Details of these methods are presented in the Examples. A preferred protein to purify according to these methods is PHIS-PDi33$_{234}$. PHIS-PDi33$_{234}$ has very low solubility in most solutions other than, for example, 8 M urea or 150 mM sorbitol. As such, developing a purification protocol was very difficult and the resultant protocol is not obvious. The ability to accomplish hydrophobic interaction chromatography was particularly surprising since urea is not a component in a hydrophobic environment.

The following examples are provided for the purposes of illustration and are not intended to limit the scope of the present invention.

EXAMPLES

Example 1

This Example describes the cloning and sequencing of a nDi33 nucleic acid molecule of the present invention. It is to be noted that the Examples include a number of molecular biology, microbiology, immunology, biochemistry and assay techniques considered to be known to those skilled in the art. Disclosure of such techniques can be found, for example, in Sambrook et al., ibid. and related references.

A *D. immitis* Di33 nucleic acid molecule was isolated by PCR amplification of adult male and female *D. immitis* cDNA libraries using primers designed by comparing the nucleic acid sequences of the coding regions of *Onchocerca volvulus* Ov33 (see, for example, Lucius et al, 1988, *J. Exp. Med.* 168, 1199–1204) and *Acanthocheilonema viteae* Av33 (see, for example, Willenbucher et al, 1993, *Mol. Biochem. Parasitol.* 57, 349–351). The designed primers were Di33-S having nucleic acid sequence 5' GCTGGATGTGTIGTIGTIGATAATAAACTGTTTGC 3' (denoted herein as SEQ ID NO:8) and Di33-A having nucleic acid sequence.5' ATATTTCTGATAIGCTGTCATTTT 3'0 (denoted herein as SEQ ID NO:9). The PCR product of about 405 bp was submitted to nucleic acid sequence analysis. That analysis indicated the PCR product, denoted herein as nDi33$_{346}$, had a size of about 346 bp and a coding strand having a nucleic acid sequence denoted herein as SEQ ID NO: 1.

Nucleic acid molecule $nDi33_{346}$ was $^{32}p$ mixed-hexamer labeled and used to probe a *D. immitis* adult female cDNA library using stringent hybridization conditions (e.g., as disclosed in Sambrook et al, ibid.). Fourteen positive plaques were PCR analyzed to identify those apparently including full-length coding regions. Nucleic acid sequencing of a nucleic acid molecule containing an apparent full-length coding region yielded SEQ ID NO:2. The nucleic acid molecule havinga coding strand of SEQ ID NO:2 as well as the complementary strand (the sequence of which is easily determined by one skilled in the art) is denoted herein as $nDi33_{750}$. SEQ ID NO:2 has GenBank Accession No. U31450.

Translation of SEQ ID NO:2 suggests that nucleic acid molecule $nDi33_{750}$ encodes a full-length *D. immitis* Di33 protein of about 234 amino acids, referred to herein as $PDi33_{234}$, represented by SEQ ID NO:3, assuming an open reading frame having an initiation (start) codon spanning from about nucleotide 24 through about nucleotide 26 of SEQ ID NO:2 and a termination (stop) codon spanning from about nucleotide 726 through about nucleotide 728 of SEQ ID NO:2. The coding region encoding $PDi33_{234}$, excluding the stop codon, is represented by nucleic acid molecule $nDi33_{702}$, having a coding strand with the nucleic acid sequence represented herein as SEQ ID NO:4. SEQ ID NO:4 appears to encode a signal peptide of about 17 amino acids as well as an apparent mature protein of about 217 amino acids, denoted herein as $PDi33_{217}$, the amino acid sequence of which is represented herein as SEQ ID NO:7. The nucleic acid molecule encoding the apparent mature protein is referred to as $nDi33_{651}$, the nucleic acid sequence of the coding strand of which is denoted herein as SEQ ID NO:6.

The deduced amino acid sequence SEQ ID NO:3 suggests a protein having a molecular weight of about 26.4 kd and an estimated pI of about 8.55. SEQ ID NO:3 is about 82% identical to the amino acid sequence of *O. volvulus* Ov33 and about 75% identical to the amino acid sequence of *A. viteae* Av33. SEQ ID NO:4 is about 81% identical to the nucleic acid sequence of the coding region of *O. volvulus* Ov33 and about 78% identical to the nucleic acid sequence of the coding region of *A. viteae* Av33.

Example 2

This Example discloses the production of a recombinant molecule and of a recombinant cell of the present invention.

Recombinant molecule pλPR-$nDi33_{708}$ containing a *D. immitis* Di33 nucleic acid molecule operatively linked to lambda phage transcriptional control sequences and to a fusion sequence encoding a poly-histidine segment was produced in the following manner. An about 708-nucleotide DNA fragment containing nucleotides spanning from about 24 through about 731 of SEQ ID NO:1, denoted herein as $nDi33_{708}$, (the coding strand of which has a nucleic acid sequence represented herein as SEQ ID NO:5) was PCR amplified from nucleic acid molecule $nDi33_{750}$, produced as described in Example 1, using the primers Di33-sen 5' GAAGGGATCCTATGAAAATTCTTTTCTGTTTCG 3' (denoted herein as SEQ ID NO:10; BamHI site in bold) and Di33-ant 5' GGACGAATTCTGTTTAATAAATTG-CAATACAGAAATGTG 3' (denoted herein as SEQ ID NO:11; EcoRI site in bold). Recombinant molecule pAPR-$nDi33_{708}$ was produced by digesting the $nDi33_{708}$-containing PCR product with BamHI and EcoRi restriction endonucleases, gel purifying the resulting fragment and directionally subcloning it into expression vector λPRcro/T2ori/RSET-B that had been cleaved with BamHI and EcoRI and gel purified. Expression vector λPRcro/T2ori/RSET-B contains the following nucleotide segments. An about 1990-bp PvuII to AatII fragment from pUC 19 containing the ampicillin resistance gene and *E. coli* of replication; an about 1000-bp PvuII to BglII fragment from pRK248cIts (available from American Type Culture Collection, Rockville, Md.) containing lambda transcriptional regulatory regions (including the gene encoding $cI^{ts}$, the promoter $p_R$, and a sequence encoding 22 amino acids of the cro protein); an about 60-bp BglII to XbaI fragment from pGEMEX-1 (available from Promega, Madison Wis.) which contains the T7 promoter; an about 166-bp XbaI to EcoRi fragment from pRSET-B (available from Invitrogen, San Diego Calif.) which contains sequences encoding the T7-S 10 translational enhancer, the $His_6$ fusion, the 14-amino acid S10 leader fusion, and an enterokinase cleavage site as well as the multiple cloning site; and an about 210-bp EcoRi to AatII fragment containing synthetic translational and transcription termination signals including the $T_1$ translation terminators in all three reading frames, an RNA stabilization sequence from *Bacillus thurengiensis* crystal protein and the $T_2$ rho-independent transcription terminator from the trpA operon.

Recombinant molecule pλPR-$nDi33_{708}$ was transformed into *E. coli* to form recombinant cell *E. coli*:pλPR-$nDi33_{708}$ using standard techniques as disclosed in Sambrook et al., ibid.

Example 3

This Example discloses the production of a Di33 protein of the present invention in a prokaryotic cell as well as the production of anti-Di33 antibodies.

Recombinant cell *E. coli*:pλPR-$nDi33_{708}$, produced as described in Example 2, was cultured in shake flasks containing an enriched bacterial growth medium containing 0.1 mg/ml ampicillin and 1% glucose at about 32° C. When the cells reached an $OD_{600}$ of about 0.6, expression of *D. immitis* $nDi33_{708}$ was induced by quickly adjusting the temperature to 42° C. and continuing cultivation of the cells for about 2 hours. Protein production was monitored by SDS PAGE of recombinant cell lysates, followed by immunoblot analysis using standard techniques. Recombinant cell *E. coli*:pλPR-$nDi33_{708}$ produced a fusion protein, denoted herein as PHIS-$PDi33_{234}$, that migrated with an apparent molecular weight of about 35 kd.

Immunoblot analysis of recombinant cell *E. coli*:pλPR-$nDi33_{708}$ lysates indicated that the about 35 kd protein was able to bind to a T7 tag monoclonal antibody (available from Novagen, Inc., Madison, Wis.) directed against the fusion portion of the recombinant PHIS-$PDi33_{234}$ fusion protein.

The PHIS-$PDi33_{234}$ histidine fusion protein was separated from *E. coli* proteins by nickel chelation chromatography and a pH gradient. Protein purification was monitored by SDS PAGE followed by Coomassie Blue staining of the column eluate fractions. Immunoblot analysis of the *E. coli*:pλPR-$nDi33_{708}$ lysate, column eluate and column void volume indicated that the PHIS-$PDi33_{234}$ 35 kd protein isolated using nickel column chromatography was able to selectively bind to a T7 tag monoclonal antibody.

A rabbit was immunized four times with PHIS-$PDi33_{234}$ that had been purified by chelation chromatography. Antisera collected from this rabbit was denoted anti-PHIS-$PDi33_{234}$ antisera.

Example 4

This Example describes the production of a recombinant Di33 protein from a prokaryotic cell.

Recombinant cell *E. coli*:pλPR-nDi33$_{651}$, produced as described in Example 2, was cultured in a manner similar to that described in Example 3. Insoluble material, apparently refractile bodies, containing PHIS-PDi33$_{234}$ protein were obtained as follows: A cell pellet was obtained from the culture using standard techniques (e.g., centrifugation). The pellet was resuspended in Buffer A (50 millimolar (mM) phosphate, 150 mM NaCl, 10 mM EDTA, 1 mM PMSF, pH 5.75) to a final volume in milliliters (ml) of 10 times the original cell paste weight in grams (g) until a homogeneous suspension was obtained. Cells in the suspension were disrupted either by lysozyme treatment (final concentration of about 0.2 milligrams (mg) lysozyme per ml volume) followed by sonication or by microfluidization (e.g., using a dynamic French press). The resulting lysate was clarified by centrifugation (e.g., Sorval 3B centrifuge, GSA rotor, at 20 K×g for 30 minutes at 25° C. The resulting pellet included the insoluble material. The insoluble material-containing pellet was washed twice in a detergent-containing solution as follows: The pellet was resuspended in Buffer B (50 mM phosphate, 150 mM NaCl, pH 5.75, plus 1% Triton X-100 and 1% deoxycholate) in a volume equivalent to that used of Buffer A. After mixing to obtain a homogeneous suspension, the suspension was centrifuged as described above and the pellet recovered. The detergent was removed by differential extraction of the pellet with 5 M urea which solubilized contaminants but not PHIS-PDi33$_{234}$. The mixture was centrifuged and the pellet recovered.

The insoluble material was containing solution as follows: The recovered pellet was resuspended in Buffer D (8 M urea, 50 mM phosphate, 150 mM NaCl, pH 5.75) in a volume equivalent to that used of Buffer A. Dithiothreitol was added to a final concentration of 10 mM. After mixing to a homogeneous suspension, the suspension was clarified by centrifugation. The Buffer D-extracted supernatant (i.e., the PHIS-PDi33$_{234}$ protein-containing solution) was collected and the pH adjusted to pH 5.75±0.25, if necessary, using phosphoric acid or sodium hydroxide.

PHIS-PDi33$_{234}$ protein was recovered, or purified, from the PHIS-PDi33$_{234}$ protein-containing solution by cation exchange chromatography. In one embodiment, the solution was applied to a SP Sepharose column pre-equilibrated with Buffer D. The column was sequentially washed with (a) Buffer D, (b) a gradient from Buffer D to 15% Buffer E (8 M urea, 50 mM phosphate, 1 M NaCl, pH 5.75), and (c) 15% Buffer E/D (i.e., 15% Buffer E/85% Buffer D). The PHIS-PDi33$_{234}$ protein was eluted from the column with 50% Buffer E/D. The PHIS-PDi33$_{234}$-containing eluate was concentrated by ultrafiltration and adjusted to 100% Buffer D. Alternatively, the eluate was adjusted to 150 mM sorbitol, concentrated by ultrafiltration and buffer exchanged to Buffer G (50 mM phosphate, 150 mM NaCl, 150 M sorbitol) slowly by multiple 50% dilution steps. By either method, the recovered PHIS-PDi33$_{234}$ protein was at least about 80% pure; approximately 1 gram of Di33 protein was obtained from about 10 liters of culture medium. This preparation is at least pure enough to use as a diagnostic reagent.

In order to further purify PHIS-PDi33$_{234}$, PHIS-PDi33$_{234}$ recovered from the SP Sepharose column was submitted to hydrophobic interaction chromatography. The PHIS-PDi33$_{234}$ eluate from the SP Sepharose column was concentrated by ultrafiltration and buffer exchanged to Buffer F (8 M urea, 50 mM phosphate, 150 mM NaCi, 0.75 M $NH_4SO_4$, pH 5.75) or diluted (1:1) slowly with Buffer Fx (8 M urea, 50 mM phosphate, 150 mM NaCl, 1.5 M $NH_4SO_4$, pH 5.75 ), then applied to a butyl sepharose column, pre-equilibrated with Buffer F. After sample application, the column was washed sequentially with (a) Buffer F, (b) a reverse gradient to 15% Buffer D, and (c) 15% Buffer D/F. The PHIS-PDi33$_{234}$ protein was eluted from the column with 50% Buffer DIF. The PHIS-PDi33$_{234}$-containing eluate was concentrated by ultrafiltration and buffer exchanged to Buffer D. The recovered PHIS-PDi33$_{234}$ protein was at least about 95% pure, appearing to be greater than 99% pure by gel analysis.

It is to be noted that PHIS-PDi33$_{234}$ has very low solubility in most solutions other than, for example, 8 M urea or 150 mM sorbitol. As such, developing a purification protocol was very difficult and the resultant protocol is not obvious. The ability to accomplish hydrophobic interaction chromatography was particularly surprising since urea is not a component in a hydrophobic environment.

Example 5

This Example describes the production of another recombinant molecule, recombinant cell, and recombinant protein of the present invention.

Recombinant molecule pλPR-nDi33$_{651}$ containing a *D. immitis* Di33 nucleic acid molecule operatively linked to lambda phage transcriptional control sequences is produced in the following manner. An about 651-nucleotide DNA fragment containing nucleotides spanning from about 75 through about 725 of SEQ ID NO:1, denoted herein as nDi33$_{651}$, (the coding strand of which has a nucleic acid sequence represented herein as SEQ ID NO:6) is PCR amplified from nucleic acid molecule nDi33$_{750}$, produced as described in Example 1, using appropriate primers that include appropriate restriction endonuclease sites for cloning into an appropriate expression vector. Recombinant molecule pλPR-nDi33$_{651}$ is produced by digesting the nDi33$_{651}$-containing PCR product with the appropriate restriction endonucleases, gel purifying the resulting fragment and directionally subcloning the fragment into an appropriately restricted expression vector containing lambda transcription control sequences similar to those in λPRcro/T2ori/RSET-B such that nDi33$_{651}$ is operatively linked to the transcription control sequences.

Recombinant molecule pλPR-nDi33$_{651}$ is transformed into *E. coli* to form recombinant cell *E. coli*:pλPR-nDi33$_{651}$ using standard techniques as disclosed in Sambrook et al., ibid.

Recombinant cell *E. coli*:pλPR-nDi33$_{651}$ can be expressed as described in Example 3 and purified using methods such as those described in Example 4 to produce an apparently mature *D. immitis* Di33 protein denoted herein as PDi33$_{217}$.

Example 6

This Example describes the ability of Di33 to detect heartworm infection in cats as early as 8 weeks post infection.

ELISAs were conducted as follows. Microtiter dish wells were coated with $PHIS-PDi33_{234}$, produced as described in Example 4, by incubating about 100 ul of 100 ng $PHIS-PDi33_{234}$ per ml of CBC buffer (50 mM carbonate/bicarbonate buffer, pH 9.6) in each well overnight at about 4° C. Solution remaining in the wells was discarded, and the wells were washed 4 times with 10 mM phosphate-buffered saline (PBS) with 0.05% Teen-20, pH 7.4 (PBST). About 100 ul of a 1:50 diluted feline serum sample (diluted in PBST) was added to each well. Each serum sample was applied in duplicate or triplicate wells. Positive and negative control samples were also applied to calibrate the assay. The samples were incubated in the Di33-coated wells for 30 minutes at room temperature, at which time solution remaining in the wells was discarded. The wells were washed 4 times with PBST. To detect binding of feline anti-Di33 IgG antibodies to Di33, about 100 ul of a 1:5000 diluted goat anti-feline IgG (H+L):HRP (i.e., goat anti-feline IgG heavy and light chain conjugated to horse radish peroxidase; available from Kirkegaard & Perry Labs Inc.(KPL), Gaithersburg, Md., Cat. No. 14-20-26) (diluted in PBST) was added to each well and allowed to incubate for 30 minutes at room temperature. Solution remaining in the wells was discarded, and the wells were washed 4 times with PBST. About 200 ul of the TMB (3,3'5'5'-tetramethylbenzidine) Microwell Peroxidase Substrate System (available from KPL, Cat. No. 50-76-04) was added to each well and incubated for 5 minutes at room temperature. About 50 ul of 2.5 N sulfuric acid was the added to each well. Absorbances were determined at 450 nm (A[450 nm]) in an automated ELISA reader.

In a first study, each of eleven cats were infected with 40 *D. immitis* third stage larvae (L3) on day 0. Serum was collected from each of the cats on days 27, 55, 83, 111, 139 and 67 post infection. The ability to detect anti-Di33 antibodies in the collected sera using a recombinant *D. immitis* Di33 protein produced as described in Examples 3 and 4 was measured by ELISA. Cats were necropsied and the number of adult worms in the heart of each cat was determined. Results from the ELISAs evaluating the sera collected from the 11 cats over time are presented in Table 1 and FIG. 1. Table 1 also indicates the number of worms found in the heart of each cat upon necropsy.

TABLE 1

| | Cats infected with *D. immitis* L3 Cat ID and ELISA Absorbance Values | | | | | | | | | | |
|---|---|---|---|---|---|---|---|---|---|---|---|
| Days PI | LAE1 | XFF2 | XF2 | HM2 | LAE3 | XEG1 | LAE7 | GF1 | ODS3 | GP2 | XJJ5 |
| 167 | 1.41 | 1.06 | 1.81 | 1.62 | 1.64 | 1.54 | 0.37 | 0.58 | 0.84 | 0.69 | 0.47 |
| 139 | 1.22 | 0.91 | 1.58 | 1.32 | 1.19 | 1.09 | 0.68 | 0.80 | 1.08 | 0.90 | 0.54 |
| 111 | 1.31 | 0.74 | 1.39 | 1.30 | 0.97 | 0.99 | 0.60 | 0.93 | 0.72 | 1.11 | 0.58 |
| 83 | 0.53 | 0.12 | 1.30 | 0.56 | 0.54 | 0.91 | 0.34 | 0.67 | 0.29 | 0.89 | 0.04 |
| 55 | 0.08 | 0.01 | 0.00 | −0.03 | 0.05 | 0.04 | 0.01 | 0.05 | −0.02 | 0.08 | 0.03 |
| 27 | 0.02 | 0.02 | 0.00 | −0.02 | 0.03 | 0.03 | 0.02 | −0.01 | 0.04 | −0.05 | 0.03 |
| 0 | 0.01 | 0.01 | 0.02 | −0.03 | 0.03 | 0.04 | 0.01 | 0.02 | −0.02 | 0.05 | 0.08 |
| HW burden | 7 | 9 | 3 | 7 | 4 | 8 | 3 | 0 | 2 | 3 | 4 |

Figure 2:
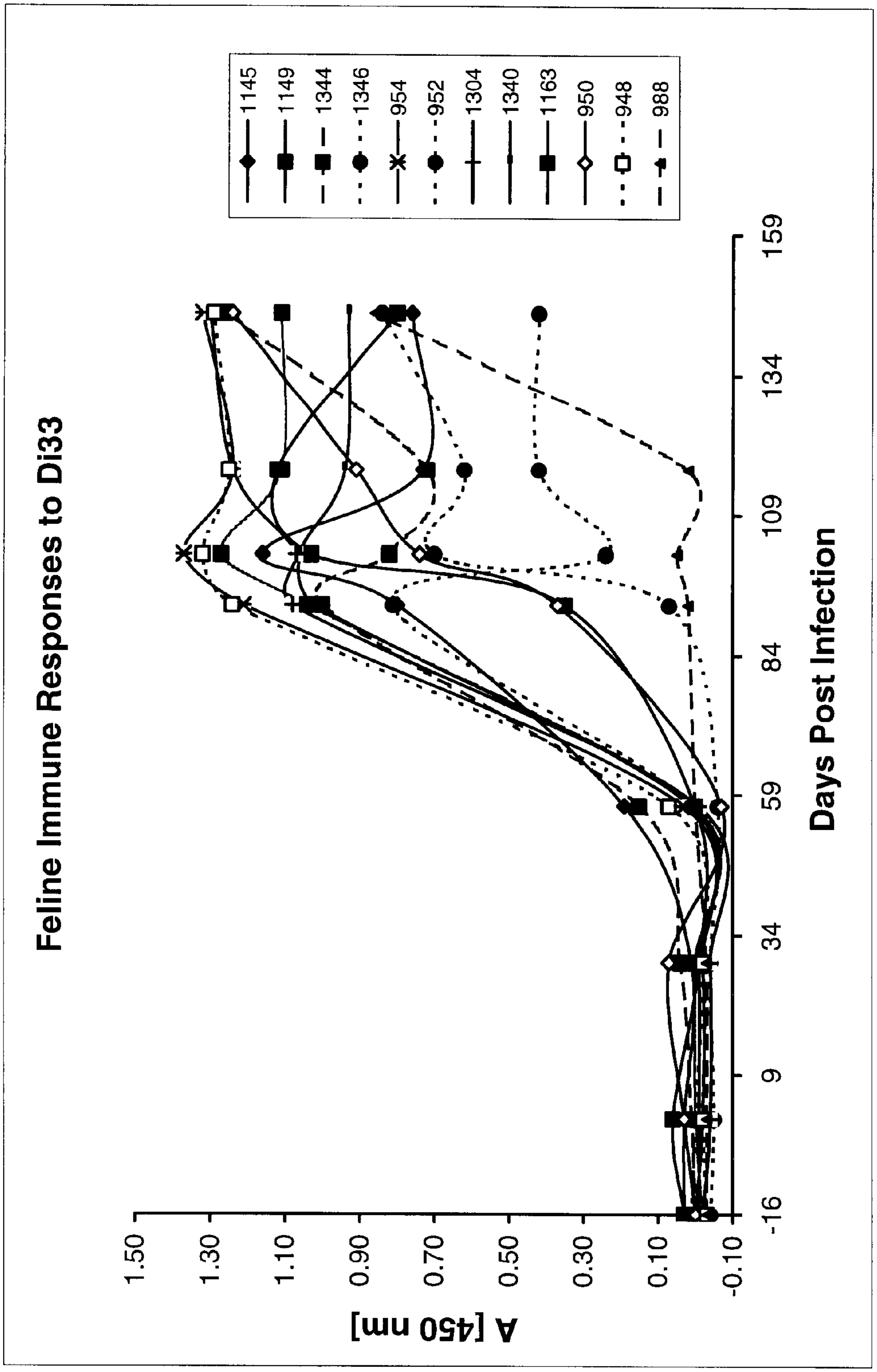
FIG. 2 depicts ELISA results using a heartworm detection reagent of the present invention to detect anti-Di33 IgG antibodies in *D. immitis*-infected cats.

In a second study, each of twelve cats were infected with 100 *D. immitis* third stage larvae (L3) on day 0. Serum was collected from each of the cats 6 days prior to infection and on days 1, 29, 57, 93, 102, 117 and 145 post-infection. The ability to detect anti-Di33 antibodies in the collected sera using a recombinant *D. immitis* Di33 protein produced as described in Examples 3 and 4 was measured by ELISA. Cats were necropsied and the number of adult worms in the heart of each cat was determined. Results from the ELISAs evaluating the sera collected from the 12 cats over time are presented in Table 2 and FIG. 2. Table 2 also indicates the number of worms found in the heart of each cat upon necropsy.

TABLE 2

| Cats infected with *D. immitis* L3 Cat ID and ELISA Absorbance values | | | | | | | | | | | | |
|---|---|---|---|---|---|---|---|---|---|---|---|---|
| Days PI | 1145 | 1149 | 1344 | 1346 | 954 | 952 | 1304 | 1340 | 1163 | 950 | 948 | 988 |
| 145 | 0.76 | 0.80 | 1.26 | 0.84 | 1.32 | 0.42 | 1.30 | 0.93 | 1.11 | 1.24 | 1.29 | 0.86 |
| 117 | 0.73 | 1.12 | 0.72 | 0.62 | 1.24 | 0.42 | 1.24 | 0.94 | 1.11 | 0.91 | 1.25 | 0.02 |
| 102 | 1.16 | 1.03 | 0.82 | 0.70 | 1.37 | 0.24 | 1.07 | 1.06 | 1.27 | 0.74 | 1.32 | 0.05 |
| 93 | 0.80 | 0.35 | 1.00 | 0.07 | 1.21 | 0.81 | 1.08 | 1.02 | 1.04 | 0.37 | 1.24 | 0.02 |
| 57 | 0.19 | 0.00 | 0.15 | −0.06 | 0.03 | 0.01 | −0.01 | 0.01 | 0.00 | −0.07 | 0.07 | 0.00 |
| 29 | 0.01 | −0.01 | 0.04 | −0.04 | −0.02 | −0.02 | −0.04 | −0.01 | 0.00 | 0.07 | −0.02 | −0.03 |
| 1 | 0.03 | 0.06 | 0.01 | −0.05 | −0.02 | 0.00 | −0.04 | −0.01 | 0.00 | 0.03 | −0.02 | −0.03 |
| −16 | 0.03 | 0.03 | 0.00 | −0.04 | 0.00 | 0.01 | −0.02 | −0.01 | −0.02 | 0.00 | −0.03 | −0.03 |
| HW burden | 1 | 4 | 1 | 2 | 11 | 1 | 11 | 13 | 1 | 3 | 12 | 0 |

The results of these studies indicate that anti-Di33 IgG antibodies are detectable in *D. immitis* cats as early as 8 weeks, and at high concentrations by 10 to 12 weeks post infection. The results also demonstrate that anti-Di33 antibodies can also be detected in animals as the *D. immitis* further develops into adults as well as in animals harboring adult heartworms.

Example 7

This Example demonstrates the ability of PDi33 to detect heartworm infection in cats infected with a single male or female worm.

In a first study, each of ten cats was infected with *D. immitis* by mosquito bites. Serum was collected from each of the cats on day 0 prior to infection and at about 2, 4 and 6 months post-infection. The ability to detect anti-Di33 antibodies in the collected sera using a recombinant *D. immitis* Di33 protein produced as described in Examples 3 and 4 was measured by ELISA as described in Example 6. In this study, absorbances were reported as absorbance units per ml (AbU/ml); AbU/ml are derived from A[450 nm] by second order polynomic regression analysis of data points plotted against a standard curve. In this case, the cut-off value is between about 4 and 6 AbU/ml. Cats were necropsied and the number of adult worms in the heart of each cat was determined. Results from the ELISAs evaluating the sera collected from the 10 cats over time are presented in Table 3, which also indicates the number of worms found in the heart of each cat upon necropsy.

TABLE 3

| Cats infected with Heartworm by Mosquito Bite | | | | |
|---|---|---|---|---|
| | | | Number of Worms | |
| Cat I.D. | Day P.I. | AbU/ml | M | F |
| GR3 | 0 MO | 0 | 1 | 0 |
| GR3 | 2 MO | 5 | | |
| GR3 | 4 MO | 65 | | |
| GR3 | 6 MO | 100 | | |
| BO1 | 0 MO | 0 | 2 | 0 |
| BO1 | 2 MO | 1 | | |
| BO1 | 4 MO | 54 | | |
| BO1 | 6 MO | 83 | | |
| CF3 | 0 MO | 0 | 0 | 2 |
| CF3 | 2 MO | 32 | | |
| CF3 | 4 MO | 100 | | |
| CF3 | 6 MO | 100 | | |

TABLE 3-continued

| Cats infected with Heartworm by Mosquito Bite | | | | |
|---|---|---|---|---|
| | | | Number of Worms | |
| Cat I.D. | Day P.I. | AbU/ml | M | F |
| NY4 | 2 MO | 3 | 0 | 2 |
| NY4 | 4 MO | 34 | | |
| NY4 | 6 MO | 100 | | |
| AEB3 | 0 MO | 4 | 0 | 3 |
| EB3 | 2 MO | 2 | | |
| EB3 | 4 MO | 100 | | |
| EB3 | 6 MO | 100 | | |
| GA2 | 0 MO | 0 | 0 | 1 |
| GA2 | 2 MO | 0 | | |
| GA2 | 4 MO | 100 | | |
| GA2 | 6 MO | 100 | | |
| V12 | 0 MO | 0 | 0 | 2 |
| V12 | 2 MO | 2 | | |
| V12 | 4 MO | 16 | | |
| V12 | 6 MO | 100 | | |
| GJ2 | 0 MO | 0 | 0 | 1 |
| GJ2 | 2 MO | 1 | | |
| GJ2 | 4 MO | 8 | | |
| GJ2 | 6 MO | 31 | | |
| WV2 | 0 MO | 1 | 1 | 1 |
| WV2 | 2 MO | 2 | | |
| WV2 | 6 MO | 43 | | |
| K3 | 0 MO | 1 | 1 | 2 |
| K3 | 6 MO | 100 | | |

In a second study, serum was collected from each of 8 cats that had been naturally infected with *D. immitis* at some stage during its life. The ability to detect anti-Di33 antibodies in the collected sera using a recombinant *D. immitis* Di33 protein produced as described in Examples 3 and 4 was measured by ELISA as described in Example 6, with absorbances being reported as absorbance units per ml (AbU/mi). The cats were necropsied and the number of adult worms in the heart of each cat was determined. Results from the ELISAs evaluating sera collected from the 8 cats are presented in Table 4, which also indicates the number of worms found in the heart of each cat.

TABLE 4

| Naturally infected cats | | | | |
|---|---|---|---|---|
| Cat I.D. | AbU/ml | M | F | immature |
| C4 | 2 | 0 | 1 | 1 |
| C6 | 17 | 0 | 1 | 0 |

TABLE 4-continued

| Naturally infected cats | | | | |
|---|---|---|---|---|
| Cat I.D. | AbU/ml | M | F | immature |
| S17 | 48 | 1 | 0 | 0 |
| S19 | 12 | 1 | 0 | 0 |
| S41 | 8 | 1 | 0 | 0 |
| S42 | 22 | 0 | 0 | 1 |
| B9 | 100 | 0 | 2 | 0 |
| B32 | 5 | 1 | 0 | 0 |

These results indicate not only that a Di33 protein can be used to detect *D. immitis* infection in a naturally-infected or mosquito-bite infected cat, but also that it is possible to detect infection in a cat in which *D. immitis* infection results in the maturation of only a single worm. Furthermore, it is possible to detect a single male worm by the Di33-based assay, unlike the circulating antigen test (see, for example, U.S. Pat. No. 4,839,275, ibid.) which can only detect female worm infection.

Example 8

This Example demonstrates the specificity of Di33 to recognize heartworm infections. Specifically, Di33 does not cross-react with *Taenia taeniaeformis, Toxocara cati*, and *Ancylostoma tubaeforme*, each of which is a parasite that infects the gastro-intestinal tract of cats.

Serum was collected from each of five cats infected with *T. taeniaeformis, T. cati*, and *A. tubaeforme* on day 0 prior to infection and at about 3, 4, 7 and 10 weeks post-infection. The ability of a recombinant *D. immitis* Di33 protein produced as described in Examples 3 and 4 to detect infection by *T. taeniaeformis, T. cati*, and/or *A. tubaeforme* was determined by ELISA as described in Example 6, with absorbances being reported as AbU/ml. Results from the ELISAs evaluating the sera collected from the 5 cats over time are presented in Table 5. The results demonstrate that recombinant Di33 protein does not cross-react with antibodies produced upon infection of cats with *T. taeniaeformis, T. cati*, or *A. tubaeforme*.

TABLE 5

| Cats infected with other G.I. parasites | | |
|---|---|---|
| Cat I.D. | Day P.I. | AbU/ml |
| NEL1 | 0 WK | 0 |
| NEL1 | 3 WK | 0 |
| NEL1 | 4 WK | 0 |
| NEL1 | 7 WK | 0 |
| NEL1 | 10 WK | 0 |
| NC01 | 0 WK | 0 |
| NC01 | 3 WK | 0 |
| NC01 | 4 WK | 0 |
| NC01 | 7 WK | 0 |
| NC01 | 10 WK | 0 |
| NCY1 | 0 WK | 0 |
| NCY1 | 3 WK | 0 |
| NCY1 | 4 WK | 2 |
| NCY1 | 7 WK | 2 |
| NCY1 | 10 WK | 0 |
| BFJ2 | 0 WK | 0 |
| BFJ2 | 3 WK | 0 |
| BFJ2 | 4 WK | 0 |
| BFJ2 | 7 WK | 0 |
| BFJ2 | 10 WK | 0 |
| BFL3 | 0 WK | 0 |
| BFL3 | 3 WK | 0 |
| BFL3 | 4 WK | 0 |
| BFL3 | 7 WK | 0 |
| BFL3 | 10 WK | 0 |

Example 9

This Example demonstrates that *D. immitis* infection stimulates the production of anti-Di33 IgE antibodies in cats and dogs. This Example also shows the ability of PDi33 to detect heartworm infection in cats and dogs by detection of anti-Di33 IgE antibodies.

ELISAs were conducted as follows. Microtiter dish wells of Immulon II plates (available from Dynatech, Inc., Chantilly, Va.) were coated overnight at 4° C. with either about 1 ug per well of PHIS-PDi33$_{234}$, produced as described in Example 4, or with about 1 ug per well of HW Ag, which refers to a heartworm antigen preparation that is the clarified supernatant of adult heartworms homogenized in PBS by adding to the wells either about 100 ul of 10 ug PHIS-PDi33$_{234}$ per ml CBC buffer (50 mM carbonate/bicarbonate buffer, pH 9.6) or about 100 ul of 10 ug HW Ag per ml CBC buffer. Solution remaining in the wells was discarded, and the wells were washed 4 times with PBST. About 100 ul of 1:10 diluted feline or canine serum (diluted in PBST with 0.25% BSA) was added to each well. Each serum sample was applied in duplicate wells. Positive and negative control samples were also applied to calibrate the assay. The samples were incubated in the Di33- or HW Ag-coated wells for 1 hour at room temperature, at which time solution remaining in the wells was discarded and the wells washed 4 times with PBST. To detect binding of feline or canine IgE antibodies to Di33 or to HW Ag, about 100 ul of a 1:4000 diluted biotinylated FcE receptor alpha chain (see, for example, U.S. Pat. No. 4,962,035, issued Oct. 9, 1990, by Leder et al), diluted in PBST with 0.25% BSA, was added to each well (about 1 ng protein per well) and allowed to incubate for 1 hour at room temperature. Solution remaining in the wells was discarded, and the wells washed 4 times with PBST. About 100 ul of a streptavidin-peroxidase complex solution diluted 1:4000 in PBST with 0.25% BSA (available from KPL, Cat. No. 14-30-00) was added to each well (about 0.125 ug per well) and incubated for 1 hour at room temperature. Solution remaining in the wells was discarded, and the wells washed 4 times with PBST. TMB substrate (available from KPL, Cat. No. 0-76-04) was added for 10 minutes, followed by stop solution (available from KPL). Optical densities (OD) were determined at 450 nm in an automated ELISA reader.

Figure 3:
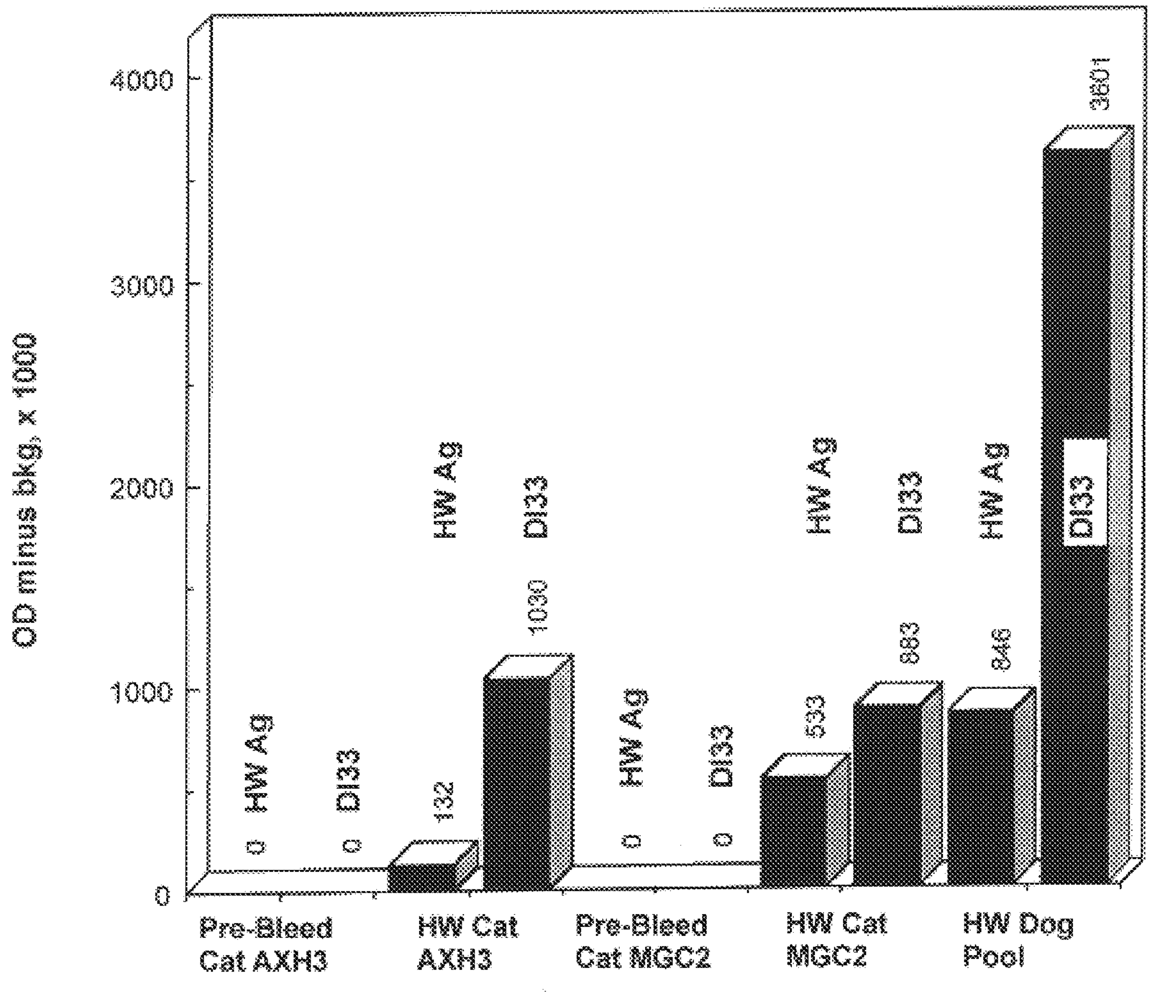
FIG. 3 depicts ELISA results using a heartworm detection reagent of the present invention to detect anti-Di33 IgE antibodies in *D. immitis*-infected cats.

The following sera were tested by ELISA for the presence of anti-Di33 or anti HW Ag IgE antibodies: sera collected from cat AXH3 90 days prior to heartworm infection (Pre-Bleed cat AXH3 sera) and 168 days post heartworm infection (HW Cat AXH3 sera); sera collected from cat MGC2 90 days prior to heartworm infection (Pre-Bleed cat MGC2 sera) and 168 days post heartworm infection (HW Cat MGC2 sera); and pooled sera from 6 dogs infected with heartworm for at least 200 days (HW Dog Pool). FIG. 3 shows that only sera collected post *D. immitis* infection had detectable levels of anti-Di33 or anti-HW Ag IgE antibodies. Such antibodies were found in cats as well as dogs infected with *D. immitis*. Furthermore, the Di33 preparation appears to be more sensitive than the HW Ag preparation in detecting IgE antibodies.

Figure 4:
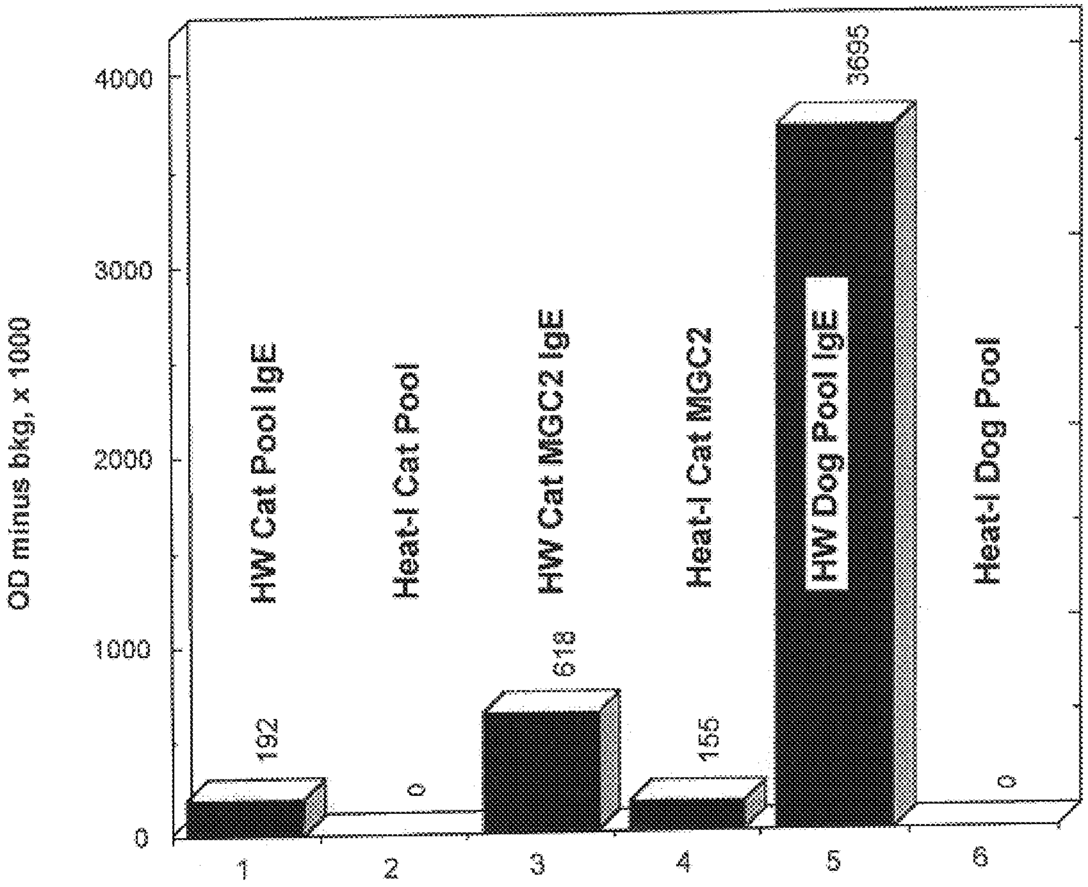
FIG. 4 depicts ELISA results using a heartworm detection reagent of the present invention to detect anti-Di33 IgE antibodies in *D. immitis*-infected cats.

In order to further demonstrate that the antibodies being detected were IgE antibodies (as opposed to, for example IgG or IgA antibodies), equivalent sera samples of (a) pooled sera from cats infected with heartworm, (b) pooled sera from dogs infected with heartworm, or (c) sera from cat MGC2 infected with heartworm, were either heated at 56° C. for 4 hours prior to the ELISA or not heated prior to the ELISA, the ELISA plates in the experiment having been pre-coated with PHIS-PDi33$_{234}$ as described above. (Note that the binding between IgE and its receptor is heat labile; i.e., Fc$_{\epsilon}$ receptor does not bind heat-treated IgE.) FIG. 4 shows the heat lability of the binding reaction, once again demonstrating that Di33 can be used to detect *D. immitis* infection in animals by detecting anti-Di33 IgE antibodies.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

SEQUENCE LISTING

The following Sequence Listing is submitted pursuant to 37 CFR §1.821. A copy in computer readable form is also submitted herewith.

Applicants assert pursuant to 37 CFR §1.821(f) that the content of the paper and computer readable copies of SEQ ID NO:1 through SEQ ID NO:11 submitted herewith are the same.

What is claimed is:

1. A method to detect *D. immitis* infection in a non-adapted host comprising:

(a) contacting a bodily fluid collected from said host with a formulation comprising a recombinant *D. immitis* Di33 protein under conditions sufficient to form an immunocomplex between said recombinant *D. immitis* Di33 protein and anti-Di33 antibodies;

(b) measuring immunocomplex formation between said recombinant *D. immitis* Di33 protein and anti-Di33 antibodies, if any, in said fluid, wherein the presence of said immunocomplex indicates that said host is or has recently been infected with *D. immitis*, wherein said recombinant *D. imminitis* Di33 protein is not cross-reactive with scrum from a host infected with an organism selected from the group consisting of *Taenia taeniaeformis, Toxocara cati*, and *Ancylostoma tubaeforme* at 10 weeks post-infection, and wherein said method detects *D. immitis* infection resulting in the maturation of a single adult heartworm.

2. The method of claim 1, wherein said method detects *D. immitis* infection in said host prior to maturation of said *D. immitis* into an adult heartworm.

3. The method of claim 1, wherein said method detects *D. immitis* infection in said host within at least ten weeks post infection of said host with *D. immitis.*

4. The method of claim 1, wherein said method detects *D. immitis* infection in a non-adapted host harboring adult heartworms.

5. The method of claim 1, wherein said method detects *D. immitis* infection resulting in the maturation of a single adult male heartworm.

6. The method of claim 1, wherein said method detects *D. immitis* infection resulting in the maturation of a single adult female heartworm.

7. The method of claim 1, wherein said host is selected from the group consisting of a cat and a ferret.

8. The method of claim 1, wherein said immunocomplex is measured by contacting said recombinant *D. immitis* Di33 protein-contacted bodily fluid with a composition that selectively binds to an antibody selected from the group consisting of an IgG anibody, an IgE antibody, an IgM antibody, and an IgA antibody.

9. The method of claim 8, wherein said composition is conjugated to a detectable marker.

10. The method of claim 8, wherein said composition is immobilized on a substrate.

11. The method of claim 1, wherein said recombinant *D. immitis* Di33 protein is immobilized on a substrate.

12. The method of claim 1, wherein said immunocomplex forms in solution.

13. The method of claim 1, wherein said step of measuring comprises an assay selected from the group consisting of an enzyme-linked immunoassay, a radioimmunoassay, a fluorescence immunoassay, a lateral flow assay, an agglutination assay, a particulate-based assay, an immonoprecipitation assay, and a immunoblotting assay.

14. The method of claim 1, wherein said recombinant *D. immitis* Di33 protein is conjugated to a detectable marker.

15. A method to detect *D. immitis* infection in a non-adapted host animal, said method comprising:

(a) contacting a bodily fluid collected from said animal with a formulation comprising a recombinant *D. immitis* Di33 protein under conditions sufficient to form an immunocomplex between said recombinant *D. immitis* Di33 protein and anti-Di33 IgE antibodies; and (b) measuring immunocomplex formation between said recombinant *D. immitis* Di33 protein and anti-Di33 IgE antibodies, if any, in said fluid, wherein the presence of said immunocomplex indicates that said animal is or has recently been infected with *D. immitis*, wherein said recombinant *D. immitis* Di33 protein is not cross-reactive with scrum from a host infected with an organism selected from the group consisting of *Taenia taeniaeformis, Toxocara cati*, and *Ancylostoma tubaeforme* at 10 weeks post-infection and wherein said method detects *D. immitis* infection resulting in the maturation of a single adult heartworm.

16. The method of claim 15, wherein said animal is selected from the group consisting of cats and ferrets.

17. The method of claim 15, wherein said method detects *D. immitis* infection in said animal within at least ten weeks post infection of said animal with *D. immitis*.

* * * * *

UNITED STATES PATENT AND TRADEMARK OFFICE

CERTIFICATE OF CORRECTION

PATENT NO. : 6,391,569 B1

DATED : May 21, 2002

INVENTOR(S) : Robert B. Grieve et al.

It is certified that error appears in the above-identified patent and that said Letters Patent is hereby corrected as shown below:

Column 39,

Line 52, please delete “imminitis” and replace with -- immitis --.

Line 53, please delete “scrum” and replace with -- serum --.

Column 41,

Line 1, please delete “immonoprecipi-” and replace with -- immunoprecipi --.

Column 42,

Line 3, please delete “scrum” and replace with -- serum --.

Signed and Sealed this

Twenty-second Day of April, 2003

JAMES E. ROGAN

*Director of the United States Patent and Trademark Office*

```
                              SEQUENCE LISTING


(1) GENERAL INFORMATION:

   (iii) NUMBER OF SEQUENCES:  11


(2) INFORMATION FOR SEQ ID NO:1:

     (i) SEQUENCE CHARACTERISTICS:
          (A) LENGTH:  346 ba se pairs
          (B) TYPE:  nucleic acid
          (C) STRANDEDNESS:  sin gle
          (D) TOPOLOGY:  linear

    (ii) MOLECULE TYPE:  cDNA

    (xi) SEQUENCE DESCRIPTION:  SEQ ID NO :1:

GAACAGCTTC TATCTTCGTG ATCTAACAAC CGAAGAGCAA AGAGAACTTG               50

CACAATATGT TGAAGATTCA AATCAATACA AAGAAGAAGT AAAGACATCA              100

TTGGAAGAAA GACGTAAAGG ATGGCAATTA GCACGACATG GTGAGAAGGA              150

TGCTAAAGTT TTATCATCAT TAGCAGAAAA GAAATTCCCA AAACCACCAA              200

AAAAACCATC ATTCTGCTCA GCTGGTGATA CGACACAATA CTATTTTGAT              250

GGTTGTATGG TTCAGAATAA TAAAATATAT GTGGGACGAA TGTATGTACG              300

TGATTTAACA TCCGATGAAA TAAATCAACT GAAAACATTT GATGCT                  346


(2) INFORMATION FOR SEQ ID NO:2:

     (i) SEQUENCE CHARACTERISTICS:
          (A) LENGTH:  750 ba se pairs
          (B) TYPE:  nucleic acid
          (C) STRANDEDNESS:  sin gle
          (D) TOPOLOGY:  linear

    (ii) MOLECULE TYPE:  cDNA

    (ix) FEATURE:
          (A) NAME/KEY:  CDS
          (B) LOCATION:  24..728

    (xi) SEQUENCE DESCRIPTION:  SEQ ID NO :2:
```

-continued

```
GAATATTTCA ACAAAATAAA ACT ATG AAA ATT CTT TTC T GT TTC            44
                          Met Lys Ile Leu Phe Cys Phe
                            1               5

GTA TTG CTT GCG ATA GCA GCA TTG CGA GCA A GC GTC ATA AAT          86
Val Leu Leu Ala Ile Ala Ala Leu Arg Ala S er Val Ile Asn
         10                  15                  20

CGA CAC AAC AAA CGT TTT GCC GGA TTC AGT G TT GCT GGA ATT         128
Arg His Asn Lys Arg Phe Ala Gly Phe Ser V al Ala Gly Ile
             25                  30                  35

GGT GGA ACT GCC GGA TGT GTT GTT GTT GAT A AT AAA CTT TTT         170
Gly Gly Thr Ala Gly Cys Val Val Val Asp A sn Lys Leu Phe
                 40                  45

GCG AAC AGC TTC TAT CTT CGT GAT CTA ACA A CC GAA GAG CAA         212
Ala Asn Ser Phe Tyr Leu Arg Asp Leu Thr T hr Glu Glu Gln
 50                  55                  60

AGA GAA CTT GCA CAA TAT GTT GAA GAT TCA A AT CAA TAC AAA         254
Arg Glu Leu Ala Gln Tyr Val Glu Asp Ser A sn Gln Tyr Lys
     65                  70                  75

GAA GAA GTA AAG ACA TCA TTG GAA GAA AGA C GT AAA GGA TGG         296
Glu Glu Val Lys Thr Ser Leu Glu Glu Arg A rg Lys Gly Trp
         80                  85                  90

CAA TTA GCA CGA CAT GGT GAG AAG GAT GCT A AA GTT TTA TCA         338
Gln Leu Ala Arg His Gly Glu Lys Asp Ala L ys Val Leu Ser
             95                 100                 105

TCA TTA GCA GAA AAG AAA TTC CCA AAA CCA C CA AAA AAA CCA         380
Ser Leu Ala Glu Lys Lys Phe Pro Lys Pro P ro Lys Lys Pro
                110                 115

TCA TTC TGC TCA GCT GGT GAT ACG ACA CAA T AC TAT TTT GAT         422
Ser Phe Cys Ser Ala Gly Asp Thr Thr Gln T yr Tyr Phe Asp
120                 125                 130

GGT TGT ATG GTT CAG AAT AAT AAA ATA TAT G TG GGA CGA ATG         464
Gly Cys Met Val Gln Asn Asn Lys Ile Tyr V al Gly Arg Met
    135                 140                 145

TAT GTA CGT GAT TTA ACA TCC GAT GAA ATA A AT CAA CTG AAA         506
Tyr Val Arg Asp Leu Thr Ser Asp Glu Ile A sn Gln Leu Lys
        150                 155                 160

ACA TTT GAT GCT AAA ATG ACA GCA TAT CAG A AA TAT TTG TCA         548
Thr Phe Asp Ala Lys Met Thr Ala Tyr Gln L ys Tyr Leu Ser
            165                 170                 175

TCG TCC ATT CAA CAG CAA GTT GAT AGC TTA T TT GGT GAT AAA         590
Ser Ser Ile Gln Gln Gln Val Asp Ser Leu P he Gly Asp Lys
                180                 185

TCA AAT CTA TTC AAT TTA TTC ACT GAT ACA C GT CAT GAA ACA         632
Ser Asn Leu Phe Asn Leu Phe Thr Asp Thr A rg His Glu Thr
190                 195                 200

TCA TCA CAA CCA TCC GAT GCT ACA ACA ATC T CG ACA ACA ACT         674
Ser Ser Gln Pro Ser Asp Ala Thr Thr Ile S er Thr Thr Thr
    205                 210                 215

CAA GCT CCA GTT GAA CCA CCC GAA ACA CCA C AT TTC TGT ATT         716
Gln Ala Pro Val Glu Pro Pro Glu Thr Pro H is Phe Cys Ile
        220                 225                 230

GCA ATT TAT TAA ACAAAAAAAA AAAAAAAAAA AA                        750
Ala Ile Tyr
```

(2) INFORMATION FOR SEQ ID NO:3:

(i) SEQUENCE CHARACTERISTICS:
(A) LENGTH: 234 am ino acids
(B) TYPE: amino ac id
(D) TOPOLOGY: linear -continued (ii) MOLECULE TYPE: protein (xi) SEQUENCE DESCRIPTION: SEQ ID NO :3:

```
Met Lys Ile Leu Phe Cys Phe Val Leu Leu A la Ile Ala Ala
  1               5                  10

Leu Arg Ala Ser Val Ile Asn Arg His Asn L ys Arg Phe Ala
 15                  20                  25

Gly Phe Ser Val Ala Gly Ile Gly Gly Thr A la Gly Cys Val
     30                  35                  40

Val Val Asp Asn Lys Leu Phe Ala Asn Ser P he Tyr Leu Arg
         45                  50                  55

Asp Leu Thr Thr Glu Glu Gln Arg Glu Leu A la Gln Tyr Val
             60                  65                  70

Glu Asp Ser Asn Gln Tyr Lys Glu Glu Val L ys Thr Ser Leu
                 75                  80

Glu Glu Arg Arg Lys Gly Trp Gln Leu Ala A rg His Gly Glu
 85                  90                  95

Lys Asp Ala Lys Val Leu Ser Ser Leu Ala G lu Lys Lys Phe
    100                 105                 110

Pro Lys Pro Pro Lys Lys Pro Ser Phe Cys S er Ala Gly Asp
        115                 120                 125

Thr Thr Gln Tyr Tyr Phe Asp Gly Cys Met V al Gln Asn Asn
            130                 135                 140

Lys Ile Tyr Val Gly Arg Met Tyr Val Arg A sp Leu Thr Ser
                145                 150

Asp Glu Ile Asn Gln Leu Lys Thr Phe Asp A la Lys Met Thr
155                 160                 165

Ala Tyr Gln Lys Tyr Leu Ser Ser Ser Ile G ln Gln Gln Val
    170                 175                 180

Asp Ser Leu Phe Gly Asp Lys Ser Asn Leu P he Asn Leu Phe
        185                 190                 195

Thr Asp Thr Arg His Glu Thr Ser Ser Gln P ro Ser Asp Ala
            200                 205                 210

Thr Thr Ile Ser Thr Thr Thr Gln Ala Pro V al Glu Pro Pro
                215                 220

Glu Thr Pro His Phe Cys Ile Ala Ile Tyr
225                 230
```

(2) INFORMATION FOR SEQ ID NO:4:

(i) SEQUENCE CHARACTERISTICS:
(A) LENGTH: 702 ba se pairs
(B) TYPE: nucleic acid
(C) STRANDEDNESS: sin gle
(D) TOPOLOGY: linear (ii) MOLECULE TYPE: cDNA (xi) SEQUENCE DESCRIPTION: SEQ ID NO :4:

```
ATGAAAATTC TTTTCTGTTT CGTATTGCTT GCGATAGCAG CATTGCGAGC    50

AAGCGTCATA AATCGACACA ACAAACGTTT TGCCGGATTC AGTGTTGCTG   100

GAATTGGTGG AACTGCCGGA TGTGTTGTTG TTGATAATAA ACTTTTTGCG   150

AACAGCTTCT ATCTTCGTGA TCTAACAACC GAAGAGCAAA GAGAACTTGC   200

ACAATATGTT GAAGATTCAA ATCAATACAA AGAAGAAGTA AAGACATCAT   250
```

-continued

```
TGGAAGAAAG ACGTAAAGGA TGGCAATTAG CACGACATGG TGAGAAGGAT            300

GCTAAAGTTT TATCATCATT AGCAGAAAAG AAATTCCCAA AACCACCAAA            350

AAAACCATCA TTCTGCTCAG CTGGTGATAC GACACAATAC TATTTTGATG            400

GTTGTATGGT TCAGAATAAT AAAATATATG TGGGACGAAT GTATGTACGT            450

GATTTAACAT CCGATGAAAT AAATCAACTG AAAACATTTG ATGCTAAAAT            500

GACAGCATAT CAGAAATATT TGTCATCGTC CATTCAACAG CAAGTTGATA            550

GCTTATTTGG TGATAAATCA AATCTATTCA ATTTATTCAC TGATACACGT            600

CATGAAACAT CATCACAACC ATCCGATGCT ACAACAATCT CGACAACAAC            650

TCAAGCTCCA GTTGAACCAC CCGAAACACC ACATTTCTGT ATTGCAATTT            700

AT                                                                702
```

(2) INFORMATION FOR SEQ ID NO:5:

(i) SEQUENCE CHARACTERISTICS:
(A) LENGTH: 708 ba se pairs
(B) TYPE: nucleic acid
(C) STRANDEDNESS: sin gle
(D) TOPOLOGY: linear (ii) MOLECULE TYPE: cDNA (xi) SEQUENCE DESCRIPTION: SEQ ID NO :5:

```
ATGAAAATTC TTTTCTGTTT CGTATTGCTT GCGATAGCAG CATTGCGAGC             50

AAGCGTCATA AATCGACACA ACAAACGTTT TGCCGGATTC AGTGTTGCTG            100

GAATTGGTGG AACTGCCGGA TGTGTTGTTG TTGATAATAA ACTTTTTGCG            150

AACAGCTTCT ATCTTCGTGA TCTAACAACC GAAGAGCAAA GAGAACTTGC            200

ACAATATGTT GAAGATTCAA ATCAATACAA AGAAGAAGTA AAGACATCAT            250

TGGAAGAAAG ACGTAAAGGA TGGCAATTAG CACGACATGG TGAGAAGGAT            300

GCTAAAGTTT TATCATCATT AGCAGAAAAG AAATTCCCAA AACCACCAAA            350

AAAACCATCA TTCTGCTCAG CTGGTGATAC GACACAATAC TATTTTGATG            400

GTTGTATGGT TCAGAATAAT AAAATATATG TGGGACGAAT GTATGTACGT            450

GATTTAACAT CCGATGAAAT AAATCAACTG AAAACATTTG ATGCTAAAAT            500

GACAGCATAT CAGAAATATT TGTCATCGTC CATTCAACAG CAAGTTGATA            550

GCTTATTTGG TGATAAATCA AATCTATTCA ATTTATTCAC TGATACACGT            600

CATGAAACAT CATCACAACC ATCCGATGCT ACAACAATCT CGACAACAAC            650

TCAAGCTCCA GTTGAACCAC CCGAAACACC ACATTTCTGT ATTGCAATTT            700

ATTAAACA                                                          708
```

(2) INFORMATION FOR SEQ ID NO:6:

(i) SEQUENCE CHARACTERISTICS:
(A) LENGTH: 651 ba se pairs
(B) TYPE: nucleic acid
(C) STRANDEDNESS: sin gle
(D) TOPOLOGY: linear (ii) MOLECULE TYPE: cDNA (ix) FEATURE:
(A) NAME/KEY: CDS
(B) LOCATION: 1..651

(xi) SEQUENCE DESCRIPTION: SEQ ID NO :6:

-continued

```
AGC GTC ATA AAT CGA CAC AAC AAA CGT TTT G CC GGA TTC AGT                  42
Ser Val Ile Asn Arg His Asn Lys Arg Phe A la Gly Phe Ser
  1               5                  10

GTT GCT GGA ATT GGT GGA ACT GCC GGA TGT G TT GTT GTT GAT                  84
Val Ala Gly Ile Gly Gly Thr Ala Gly Cys V al Val Val Asp
 15                  20                  25

AAT AAA CTT TTT GCG AAC AGC TTC TAT CTT C GT GAT CTA ACA                 126
Asn Lys Leu Phe Ala Asn Ser Phe Tyr Leu A rg Asp Leu Thr
     30                  35                  40

ACC GAA GAG CAA AGA GAA CTT GCA CAA TAT G TT GAA GAT TCA                 168
Thr Glu Glu Gln Arg Glu Leu Ala Gln Tyr V al Glu Asp Ser
         45                  50                  55

AAT CAA TAC AAA GAA GAA GTA AAG ACA TCA T TG GAA GAA AGA                 210
Asn Gln Tyr Lys Glu Glu Val Lys Thr Ser L eu Glu Glu Arg
             60                  65                  70

CGT AAA GGA TGG CAA TTA GCA CGA CAT GGT G AG AAG GAT GCT                 252
Arg Lys Gly Trp Gln Leu Ala Arg His Gly G lu Lys Asp Ala
                 75                  80

AAA GTT TTA TCA TCA TTA GCA GAA AAG AAA T TC CCA AAA CCA                 294
Lys Val Leu Ser Ser Leu Ala Glu Lys Lys P he Pro Lys Pro
 85                  90                  95

CCA AAA AAA CCA TCA TTC TGC TCA GCT GGT G AT ACG ACA CAA                 336
Pro Lys Lys Pro Ser Phe Cys Ser Ala Gly A sp Thr Thr Gln
    100                 105                 110

TAC TAT TTT GAT GGT TGT ATG GTT CAG AAT A AT AAA ATA TAT                 378
Tyr Tyr Phe Asp Gly Cys Met Val Gln Asn A sn Lys Ile Tyr
        115                 120                 125

GTG GGA CGA ATG TAT GTA CGT GAT TTA ACA T CC GAT GAA ATA                 420
Val Gly Arg Met Tyr Val Arg Asp Leu Thr S er Asp Glu Ile
            130                 135                 140

AAT CAA CTG AAA ACA TTT GAT GCT AAA ATG A CA GCA TAT CAG                 462
Asn Gln Leu Lys Thr Phe Asp Ala Lys Met T hr Ala Tyr Gln
                145                 150

AAA TAT TTG TCA TCG TCC ATT CAA CAG CAA G TT GAT AGC TTA                 504
Lys Tyr Leu Ser Ser Ser Ile Gln Gln Gln V al Asp Ser Leu
155                 160                 165

TTT GGT GAT AAA TCA AAT CTA TTC AAT TTA T TC ACT GAT ACA                 546
Phe Gly Asp Lys Ser Asn Leu Phe Asn Leu P he Thr Asp Thr
    170                 175                 180

CGT CAT GAA ACA TCA TCA CAA CCA TCC GAT G CT ACA ACA ATC                 588
Arg His Glu Thr Ser Ser Gln Pro Ser Asp A la Thr Thr Ile
        185                 190                 195

TCG ACA ACA ACT CAA GCT CCA GTT GAA CCA C CC GAA ACA CCA                 630
Ser Thr Thr Thr Gln Ala Pro Val Glu Pro P ro Glu Thr Pro
            200                 205                 210

CAT TTC TGT ATT GCA ATT TAT                                             651
His Phe Cys Ile Ala Ile Tyr
                215
```

(2) INFORMATION FOR SEQ ID NO:7:

(i) SEQUENCE CHARACTERISTICS:
(A) LENGTH: 217 am ino acids
(B) TYPE: amino ac id
(D) TOPOLOGY: linear (ii) MOLECULE TYPE: protein (xi) SEQUENCE DESCRIPTION: SEQ ID NO :7:

```
Ser Val Ile Asn Arg His Asn Lys Arg Phe A la Gly Phe Ser
  1               5                  10
```

-continued

```
Val Ala Gly Ile Gly Gly Thr Ala Gly Cys V al Val Val Asp
 15                  20                  25

Asn Lys Leu Phe Ala Asn Ser Phe Tyr Leu A rg Asp Leu Thr
     30                  35                  40

Thr Glu Glu Gln Arg Glu Leu Ala Gln Tyr V al Glu Asp Ser
         45                  50                  55

Asn Gln Tyr Lys Glu Glu Val Lys Thr Ser L eu Glu Glu Arg
             60                  65                  70

Arg Lys Gly Trp Gln Leu Ala Arg His Gly G lu Lys Asp Ala
                 75                  80

Lys Val Leu Ser Ser Leu Ala Glu Lys Lys P he Pro Lys Pro
 85                  90                  95

Pro Lys Lys Pro Ser Phe Cys Ser Ala Gly A sp Thr Thr Gln
    100                 105                 110

Tyr Tyr Phe Asp Gly Cys Met Val Gln Asn A sn Lys Ile Tyr
        115                 120                 125

Val Gly Arg Met Tyr Val Arg Asp Leu Thr S er Asp Glu Ile
            130                 135                 140

Asn Gln Leu Lys Thr Phe Asp Ala Lys Met T hr Ala Tyr Gln
                145                 150

Lys Tyr Leu Ser Ser Ser Ile Gln Gln Gln V al Asp Ser Leu
155                 160                 165

Phe Gly Asp Lys Ser Asn Leu Phe Asn Leu P he Thr Asp Thr
    170                 175                 180

Arg His Glu Thr Ser Ser Gln Pro Ser Asp A la Thr Thr Ile
        185                 190                 195

Ser Thr Thr Thr Gln Ala Pro Val Glu Pro P ro Glu Thr Pro
            200                 205                 210

His Phe Cys Ile Ala Ile Tyr
                215
```

(2) INFORMATION FOR SEQ ID NO:8:

(i) SEQUENCE CHARACTERISTICS:
(A) LENGTH: 35 bas es
(B) TYPE: nucleic acid
(C) STRANDEDNESS: sin gle
(D) TOPOLOGY: linear (ii) MOLECULE TYPE: primer (ix) FEATURE:
(A) NAME/KEY: N=IN OSINE
(B) LOCATION: 12

(ix) FEATURE:
(A) NAME/KEY: N=IN OSINE
(B) LOCATION: 15

(ix) FEATURE:
(A) NAME/KEY: N=IN OSINE
(B) LOCATION: 18

(xi) SEQUENCE DESCRIPTION: SEQ ID NO :8:

GCTGGATGTG TNGTNGTNGA TAATAAACTG TTTGC 35

(2) INFORMATION FOR SEQ ID NO:9:

(i) SEQUENCE CHARACTERISTICS:
(A) LENGTH: 24 bas es
(B) TYPE: nucleic acid

-continued

```
        (C) STRANDEDNESS:  sin gle
        (D) TOPOLOGY:  linear

   (ii) MOLECULE TYPE:  primer

   (ix) FEATURE:
        (A) NAME/KEY:  N=IN OSINE
        (B) LOCATION:  13

   (xi) SEQUENCE DESCRIPTION:  SEQ ID NO :9:

ATATTTCTGA TANGCTGTCA TTTT                                            24


(2) INFORMATION FOR SEQ ID NO:10:

    (i) SEQUENCE CHARACTERISTICS:
        (A) LENGTH:  33 bas es
        (B) TYPE:  nucleic acid
        (C) STRANDEDNESS:  sin gle
        (D) TOPOLOGY:  linear

   (ii) MOLECULE TYPE:  primer

   (xi) SEQUENCE DESCRIPTION:  SEQ ID NO :10:

GAAGGGATCC TATGAAAATT CTTTTCTGTT TCG                                  33


(2) INFORMATION FOR SEQ ID NO:11:

    (i) SEQUENCE CHARACTERISTICS:
        (A) LENGTH:  39 bas es
        (B) TYPE:  nucleic acid
        (C) STRANDEDNESS:  sin gle
        (D) TOPOLOGY:  linear

   (ii) MOLECULE TYPE:  primer

   (xi) SEQUENCE DESCRIPTION:  SEQ ID NO :11:

GGACGAATTC TGTTTAATAA ATTGCAATAC AGAAATGTG                            39
```